United States Patent
Aebi et al.

(10) Patent No.: US 10,632,127 B2
(45) Date of Patent: Apr. 28, 2020

(54) TARGETED NOTCH PATHWAY INHIBITORS

(71) Applicant: Hoffmann-La Roche Inc., Little Falls, NJ (US)

(72) Inventors: Johannes Aebi, Basel (CH); Alexander Flohr, Basel (CH); Juillerat-Jeanneret Lucienne, Lausanne (CH); Golshayan Dela, Lausanne (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/837,199

(22) Filed: Dec. 11, 2017

(65) Prior Publication Data

US 2018/0200262 A1    Jul. 19, 2018

Related U.S. Application Data

(63) Continuation of application No. PCT/EP2016/062826, filed on Jun. 7, 2016.

(30) Foreign Application Priority Data

Jun. 11, 2015 (EP) .................................... 15171592

(51) Int. Cl.
  *A61K 31/553* (2006.01)
  *C07D 267/14* (2006.01)
  *A61K 47/64* (2017.01)

(52) U.S. Cl.
  CPC ............ *A61K 31/553* (2013.01); *A61K 47/64* (2017.08); *C07D 267/14* (2013.01)

(58) Field of Classification Search
  CPC ..... A61K 31/553; A61K 47/64; C07D 267/14
  See application file for complete search history.

(56) References Cited

FOREIGN PATENT DOCUMENTS

WO    2006/061136 A2    6/2006

OTHER PUBLICATIONS

ISR and Written Opinion of PCT/EP2016/062826 (dated Aug. 10, 2016).
J.C. Drieman et al., "Renal selective N-acetyl-L-γ-glutamyl prodrugs:studies on the selectivity of some model prodrugs" British Jouranal of Pharmacology 108(1):204-208 (1993).
Lucienne Juillerat-Jeanneret et al., "Target γ-Secretase Inhibition to control the Notch Pathway in Renal Diseases" Journal of Medicinal Chemistry 58(20):8097-8109 (Sep. 30, 2015).
M.E.M. Dolman et al., "Drug targeting to the kidney: Advances in the active targeting of therapeutics to proximal tubular cells" Advanced Drug Delivery Reviews 62:1344-1357 ( 2010).

*Primary Examiner* — Noble E Jarrell
(74) *Attorney, Agent, or Firm* — Genentech Inc.; Richard G.A. Bone

(57) ABSTRACT

The instant invention relates to novel conjugates of the compound of formula (I):

$$S\text{—}L\text{—}A \qquad (I)$$

or salts thereof, wherein A is a γ-secretase inhibitor, L is a linker and S is a peptidase-specific substrate, as well as processes for their manufacture, pharmaceutical compositions comprising them, and their use as medicaments.

14 Claims, 4 Drawing Sheets

TARGETED NOTCH PATHWAY INHIBITORS

CROSS-REFERENCE TO RELATED APPLICATIONS

This application is a continuation of, and claims priority to, International Patent Application No. PCT/EP2016/062826, filed on Jun. 7, 2016. This application also claims priority to European Patent Application No. 15171592.7, filed on Jun. 11, 2015. The entire contents of each of the above patent applications are hereby incorporated by reference.

The present invention relates to a conjugate of formula (I):

S—L—A  (I)

or a pharmaceutically acceptable salt thereof, wherein A is a γ-secretase inhibitor, L is a linker and S is a peptidase-specific substrate, as well as processes for their manufacture, pharmaceutical compositions comprising them, and their use as medicaments.

BACKGROUND OF THE INVENTION

Targeted therapeutics have gained prominence offering improved potency and reduced toxicity. There are two possibilities to specifically target an organ: first via a receptor expressed specifically in the target-organ or second via an enzyme with higher expression or higher activity in this organ. These concepts can be combined for even better targeting.

Tissue targeting is a critical topic of pharmaceutical investigation, in order to maximize the desired therapeutic effect whilst minimizing toxic side events, i.e. to improve the therapeutic index. Renal-specific drug targeting can be an attractive option to:

Avoid undesirable extra-renal effects
The intra-renal transport of a drug may not be optimal in relation to the target cell within the organ
Some drugs are largely inactivated before they reach the site of action in the kidneys
Pathological conditions such as abnormalities in glomerular filtration, tubular secretion, or the occurrence of proteinuria can affect the normal renal distribution of the drug.

Furthermore, cell-specific drug targeting within the kidney may provide a tool in understanding certain mechanisms of drug action and thus also to manipulate renal physiology.

Within the kidney, injury to the podocytes is the initiating cause of many renal diseases, leading to proteinuria with possible progression to end-stage renal disease. The podocyte plays a key role both in maintenance of the glomerular filtration barrier and in glomerular structural integrity. Drug targeting to the podocyte imposes two important challenges: (1) to target the right cell (where an understanding of the anatomy of the podocyte and how it interacts with surrounding cells and structures is crucial) and (2) to select and address the right pharmacological pathway and which events lead to podocyte damage.

In parallel to podocyte injury leading to glomerulosclerosis, tubulointerstitial fibrosis is another hallmark of Acute Kidney Injury (AKI) and once again, drug targeting to the proximal tubular cells may offer new tools for its treatment, by reducing toxicity of drugs that exert unwanted side effects and/or by increasing the renal efficacy of antifibrotic drugs.

Recent advanced knowledge on renal diseases has yielded several candidate pathways for designing cell-targeted therapeutics, which include the Notch pathway. Within the kidney, injury to glomerular or tubular cells is the initiating cause of many acute and chronic diseases, leading to progressive dysfunction and end-stage renal disease. The glomerulus is the main filtration barrier that determines global kidney function. Inflammatory and non-inflammatory stresses affect the glomerulus and lead to alterations in its structure, thus in its permeability and function, leading to Chronic Kidney Disease (CKD). Injury to the tubulo-interstitial tissue is a major cause of Acute Kidney Injury (AKI) in particular in weakened hospitalized patients.

Acute Kidney Injury (AKI) is a risk factor for progressive to Chronic Kidney Disease (CKD), a serious clinical condition with no effective treatment, associated with patient's high morbidity including cardiovascular and metabolic complications. Kidney diseases can be primary or occur as part of multisystemic genetic, inflammatory, autoimmune, toxic or metabolic disorders. Three main structures can be affected in the kidney, the glomerulus, the tubulo-interstitial tissue or the vessels, leading to distinct clinical syndromes in the early stages of the disease. However, irrespective to the initial insult, disease progression will lead to irreversible glomerulosclerosis and tubulo-interstitial fibrosis, thus eventual end-stage renal disease requiring dialysis or kidney transplantation. Current therapies mainly aim at treating the primary disease to limit CKD progression. Previous studies have found that genes belonging to the Notch pathway were up-regulated in kidney samples from patients and in animal models of renal disease.

Notch is a membrane inserted protein, with its active part toward the intracellular space. The enzyme γ-secretase is a large protease complex composed of two aspartyl protease catalytic subunits (presenilin-1 and -2) and three support subunits (Pen-2, Aph-1 and nicastrin), all being membrane proteins. Substrates of γ-secretase first bind to nicastrin, then are transferred between the two presenilin subunits to the γ-secretase which performs an intra-membrane hydrolysis. The γ-secretase complex is able to activate Notch by hydrolyzing a peptide bond of the Notch protein at an intra-membrane site, allowing the cleaved Notch intracellular domain to migrate to the nucleus where it activates responsive genes. The intra-membrane activity of the γ-secretase has also been involved in the release from the membrane of other biologically relevant membrane proteins involved in normal and pathological processes, including insulin-like growth factor or sorting receptors. Therefore, for selective therapy, it is mandatory to achieve only localized inhibition of this activity, thus protecting the other functions of this enzyme and of the Notch pathway in particular.

The Notch pathway has been reported to participate in renal diseases and tissue damage in the kidney, thus being a potential target to treat renal diseases. However, as the γ-secretase and the Notch pathway are also important in controlling the function of other cells, including normal cells, it is necessary to develop tools for specifically targeting Notch antagonists to diseased kidney cells.

Genetic studies performed in mice with conditional expression of the active Notch1 protein showed massive glomerulosclerosis, leading ultimately to renal failure and death of the animals. Genetic deletion of Notch transcriptional binding partner as well as treatment with γ-secretase inhibitors, thus inhibiting the γ-secretase-mediated Notch activation and translocation to the nucleus, protected the animals from nephrotic syndrome. Thus, targeted pharmacologic inhibition of the Notch pathway signaling may prevent kidney damage in a variety of diseases. Regulation of the Notch pathway signaling mainly occurs at the levels of ligand binding and γ-secretase complex-mediated cleavage. Then, cleaved Notch migrates to the nucleus where it activates responsive genes, which include Notch1 itself.

γ-Secretase inhibiting compounds and preparation thereof have for example been described in WO 2006/061136 A2. Therein disclosed (6,7,8,9-tetrahydro-5-oxa-9-aza-benzocyclohepten-7-yl)-malonamide derivatives have been reported to be useful in the treatment of Alzheimer's disease or common cancers including but not limited to cervical carcinomas and breast carcinomas and malignancies of the hematopoietic system.

For the preparation of drug-carrier conjugates the commonly applied approach is to couple the drug covalently to the carrier. The characteristics of the bond between the drug and carrier system greatly influence the in vivo behavior of the drug-carrier conjugate. The conjugate needs to be stable in the circulation to prevent premature loss of the free drug, i.e. before the carrier has been accumulated in the intended target cells. But after its accumulation, quantitative release of the drug from the carrier and regeneration of the parent drug is desired.

Herein we describe a novel therapeutic strategy aimed to locally increase the concentration of γ-secretase inhibitors as Notch antagonists in the kidney by preparing prodrugs of γ-secretase inhibitor(s) coupled to substrates for specific hydrolytic enzyme-activities expressed at high levels by specific cells in injured kidneys. The ideal prodrug would be i) inactive on γ-secretase and ii) liberated only in the kidney to have no or very low exposure of parent in plasma, and e.g. in liver, to improve the safety (margin) window.

As is evidenced herein by in vitro assays as well as a mouse model of acute kidney tubulo-interstitial disease, the γ-secretase inhibiting pay-load is selectively liberated from the prodrug in the kidney exerting a regulatory effect on the Notch pathway. Our approach involves Ac-γ-Glu prodrugs of a γ-secretase inhibitor, targeting the γ-glutamyltranspeptidase (γ-GT) and/or a specific transporter in the kidney, and the intracellular N-acylamine acid deacylase (ACY1) and γ-glutamylcyclotransferase (γ-GCT) to selectively control the activation of the Notch pathway in the context of kidney disease. We could show that such an approach was able to improve the stability of the therapeutics and the selectivity for the diseased kidney of the designed prodrugs potentially opening the way for improving treatment and decreasing side-effects of therapies aimed at controlling the Notch pathway for patients with acute and chronic kidney disorders.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "stereoisomer" denotes a compound that possesses identical molecular connectivity and bond multiplicity, but which differs in the arrangement of its atoms in space.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The term "halo", "halogen", and "halide" are used interchangeably herein and denote fluoro, chloro, bromo, or iodo. Particular example of halogen is fluoro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular example of alkyl is methyl The term "alkenyl" denotes a monovalent linear or branched hydrocarbon group of 2 to 7 carbon atoms with at least one double bond. In particular embodimets, alkenyl has 2 to 4 carbon atoms with at least one double bond. Examples of alkenyl include ethenyl, propenyl, prop-2-enyl, isopropenyl, n-butenyl, and iso-butenyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl are —$CH_2$—$CF_3$, —$CH_2$—$CH_2$—$CF_3$ or —$CH_2$—$CF_2$—$CF_3$, most particularly —$CH_2$—$CF_2$—$CF_3$.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl. Particular example of hydroxyalkyl is —$CH_2$—$CH_2$—OH.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "animal" as used herein comprises human beings and non-human animals. In one embodiment, a "non-human animal" is a mammal, for example a rodent such as rat or a mouse. In one embodiment, a non-human animal is a mouse.

The term "half maximal inhibitory concentration" (IC50) denotes the concentration of a particular compound or molecule required for obtaining 50% inhibition of a biological process in vitro. IC50 values can be converted logarithmically to pIC50 values (−log IC50), in which higher values indicate exponentially greater potency. The IC50 value is not an absolute value but depends on experimental conditions e.g. concentrations employed. The IC50 value can be converted to an absolute inhibition constant (Ki) using the Cheng-Prusoff equation (Biochem. Pharmacol. (1973) 22:3099).

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

In detail, the present invention relates a conjugate of formula (I)

or a pharmaceutically acceptable salt thereof, wherein A is a γ-secretase inhibitor with hydroxy moiety, L is a cleavable linker and S is a peptidase-specific substrate.

In a particular embodiment of the invention, A is a γ-secretase inhibitor with hydroxy-moiety.

In a particular embodiment of the invention, L is a cleavable linker, particularly an aminoethyl-carbamate linker.

In a particular embodiment of the invention, S is a recognition motif/targeting vector/peptidase-specific substrate, particularly for a transporter, for γ-glutamyl transpeptidase-specific substrate (γ-GT, EC 2.3.2.2), γ-glutamylcyclotransferase (γ-GCT, EC 2.3.2.4) and/or a (glutamyl) aminopeptidase A-specific substrate (APA, EC 3.4.11.7)

In one embodiment of the invention, A is a moiety of formula (A1)

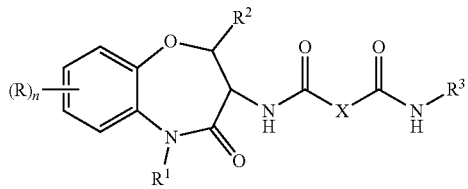

wherein

X is —CR$^4$R$^{4'}$— or —CR$^4$R$^{4'}$—O—;

R is halogen, C$_{1-7}$ alkyl or C$_{1-7}$ alkyl substituted by halogen;

R$^1$ is hydrogen, C$_{1-7}$ alkyl, C$_{1-7}$ alkyl substituted by halogen or hydroxy, C$_{1-7}$ alkenyl, —(CH$_2$)$_m$—C$_{3-8}$ cycloalkyl, —(CH$_2$)$_m$—COR', —(CH$_2$)$_m$-morpholinyl, benzyl, or benzyl substituted by halogen;

R' is C$_{1-7}$ alkoxy, hydroxy or amino;

R$^2$ is hydrogen, C$_{1-7}$ alkyl, C$_{1-7}$ alkyl substituted by halogen or hydroxy, or is benzyl or C$_{3-8}$ cycloalkyl;

R$^3$ is C$_{1-7}$ alkyl, C$_{1-7}$ alkyl substituted by halogen, is benzyl, benzyl substituted by two halogen, is —(CH$_2$)$_m$—C$_{3-8}$cycloalkyl or —(CH$_2$)$_m$-pyridinyl;

R$^4$ and R$^{4'}$ are independently from each other hydrogen, halogen, C$_{1-7}$ alkyl, C$_{1-7}$ alkyl substituted by hydroxy, C$_{1-7}$ alkoxy, or hydroxy;

n is 0, 1 or 2;

m is 0, 1 or 2;

with the proviso that at least one of R$^1$, R$^2$, R$^4$ or R$^{4'}$ is hydroxy or C$_{1-7}$ alkyl substituted by hydroxy;

wherein L is bound to A at a hydroxy-group of R$^1$, R$^2$, R$^4$ or R$^{4'}$.

Compounds of formula (A1) and preparation thereof have been described in WO 2006/061136 A2 which is herewith incorporated by reference. Compounds of formula (A1) have been described in WO 2006/061136 A2 to be γ-secretase inhibitors as has been evidenced by in vitro IC50 data on pages 17-18. Compounds of formula (A1) have been disclosed in WO 2006/061136 A2 to be useful in the treatment of Alzheimer's disease or common cancers.

In a particular embodiment of the invention, L is bound to A at a hydroxy-group of R$^1$.

In one embodiment of the invention X is —CH$_2$—, —CHCH$_3$—, —CH(CH$_2$CH$_3$)—, —C(CH$_3$)$_2$—, —C(CH$_3$)(OH)—, —C(CH$_2$CH$_3$)(OH)—, —CH(OCH$_3$)— or —C(CH$_3$)$_2$—O—.

In one embodiment of the invention X is —C(CH$_3$)$_2$—, —C(CH$_3$)(OH)—, or —C(CH$_2$CH$_3$)(OH)—.

In a particular embodiment of the invention X is —C(CH$_3$)(OH)—.

In one embodiment of the invention R is halogen, particularly fluoro.

In one embodiment of the invention n is 1.

In one embodiment of the invention R$^1$ is hydrogen, C$_{1-7}$ alkyl substituted by halogen or C$_{1-7}$ alkyl substituted by hydroxy, particularly C$_{1-7}$ alkyl substituted by hydroxy.

In one embodiment of the invention R$^1$ is hydrogen, —CH$_2$—CF$_3$ or —CH$_2$—CH$_2$—OH, particularly R$^1$ is —CH$_2$—CH$_2$—OH.

In one embodiment of the invention R$^2$ is C$_{1-7}$ alkyl, C$_{1-7}$ alkyl substituted by hydroxy, or C$_{3-8}$ cycloalkyl, particularly R$^2$ is C$_{1-7}$ alkyl.

In one embodiment of the invention R$^2$ is methyl, ethyl, hydroxy-ethyl or cyclopropyl, particularly R$^2$ is methyl.

In one embodiment of the invention R$^3$ is C$_{1-7}$ alkyl substituted by halogen, particularly R$^3$ is C$_{1-7}$ alkyl substituted by 3 or 5 fluoro.

In one embodiment of the invention R$^3$ is —CH$_2$—CF$_3$, —CH$_2$—CH$_2$—CF$_3$ or —CH$_2$—CF$_2$—CF$_3$, particularly R$^3$ is —CH$_2$—CF$_2$—CF$_3$.

In one embodiment of the invention, A is a moiety of formula (A2)

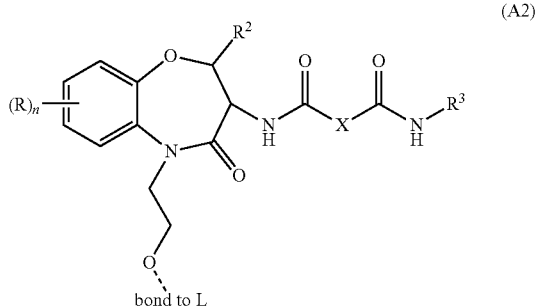

(A2)

wherein X, R, n, R² and R³ are as described herein.

In one embodiment of the invention, A is a moiety of formula (A3)

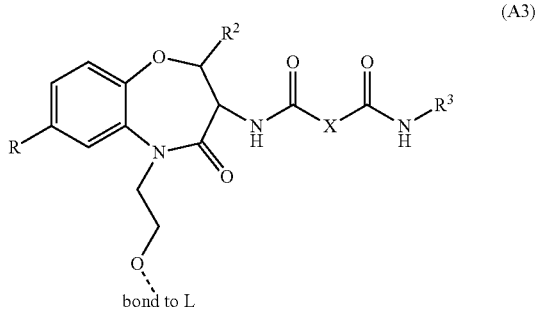

(A3)

wherein X, R, R² and R³ are as described herein.

In one embodiment of the invention, A is a moiety of formula (A4)

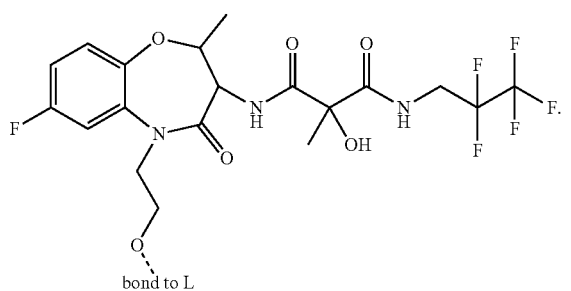

(A4)

In one embodiment of the invention, A is a moiety of formula (A5)

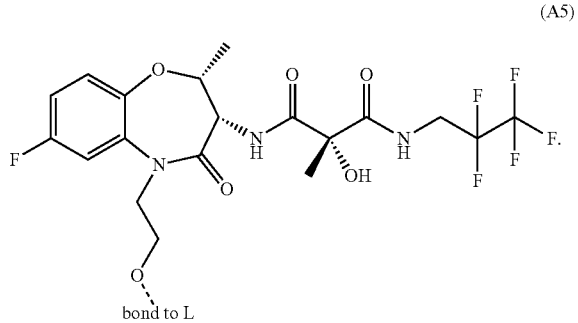

(A5)

A particular embodiment of the invention relates to a conjugate of formula (I) or a pharmaceutically acceptable salt thereof, wherein moiety A is selected from the list of:

N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide;

N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide;

(S)—N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide;

(R)—N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide;

(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide;

(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide;

(S)—N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide;

(R)—N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide;

(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide;

(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide;

N-[(6S,7R)-6-Ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide;

(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide;

(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide;

(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide;

(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide;

(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide;

(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide;

(R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide;

(S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide;

(R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide;

(S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide;

N-[(6R,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

N-[(6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

(S)—N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(R)—N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(S)—N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(R)—N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

N-[(6R,7R) or (6S,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

N-[(6S,7S) or (6R,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

(S)—N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide; and (R)—N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide;

wherein L is bound to A at a hydroxy-group and wherein L and S are as described herein.

In one embodiment of the invention, L is a moiety of formula (L1)

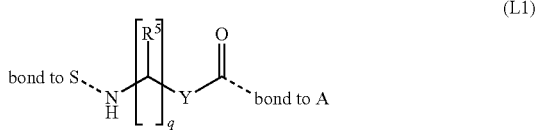

(L1)

wherein
Y is void, O or NH;
$R^5$ is hydrogen, halogen, $C_{1-7}$ alkyl, or $C_{1-7}$ alkoxy;
q is 1, 2, 3 or 4.

In one embodiment of the invention Y is NH.
In one embodiment of the invention $R^5$ is hydrogen.
In one embodiment of the invention q is 2.
In a particular embodiment of the invention L is a moiety of formula (L1) wherein Y is NH, $R^5$ is hydrogen and q is 2.

In a particular embodiment of the invention L is a moiety of formula (L2)

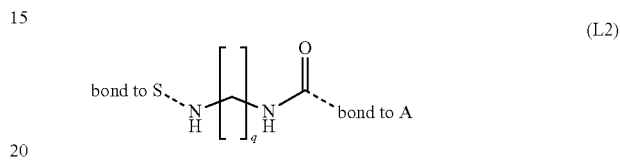

(L2)

wherein q is 1, 2 or 3, particularly q is 2.

In one embodiment of the invention S is a moiety of formula (S1)

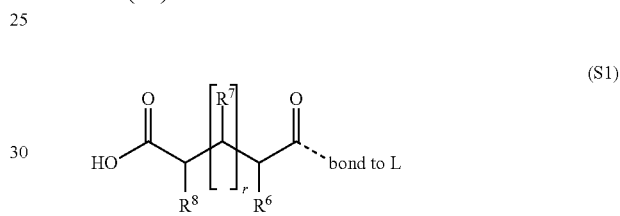

(S1)

wherein
$R^6$ is hydrogen, $C_{1-7}$ alkyl, —$NH_2$ or —NH—C(O)—$C_{1-7}$ alkyl;
each $R^7$ is independently selected from hydrogen, halogen, $C_{1-7}$ alkyl, or $C_{1-7}$ alkoxy;
$R^8$ is hydrogen, $C_{1-7}$ alkyl, —$NH_2$ or —NH—C(O)—$C_{1-7}$ alkyl;
r is 0, 1, 2 or 3;
with the proviso that at least one of $R^6$ or $R^8$ is —$NH_2$ or —NH—C(O)—$C_{1-7}$ alkyl.

In one embodiment of the invention, one of $R^6$ or $R^8$ is —$NH_2$ or —NH—C(O)—$C_{1-7}$ alkyl and the other one of $R^6$ or $R^8$ is hydrogen or $C_{1-7}$ alkyl.

In one embodiment of the invention, one of $R^6$ or $R^8$ is —$NH_2$ or —NH—C(O)—$CH_3$ and the other one of $R^6$ or $R^8$ is hydrogen.

In one embodiment of the invention $R^7$ is hydrogen.
In one embodiment of the invention r is 0 or 1, particularly 1.

In a particular embodiment of the invention $R^7$ is hydrogen and r is 1.

In a particular embodiment of the invention, S is a moiety of formula (S1) wherein $R^6$ is hydrogen, $R^7$ is hydrogen, $R^8$ is —$NH_2$ or —NH—C(O)—$C_{1-7}$ alkyl, and r is 1.

In a particular embodiment of the invention, S is a moiety of formula (S1) wherein $R^6$ is hydrogen, $R^7$ is hydrogen, $R^8$ is —$NH_2$ or —NH—C(O)—$CH_3$, and r is 1.

In a particular embodiment of the invention, S is a moiety of formula (S1) wherein $R^6$ is hydrogen, $R^7$ is hydrogen, $R^8$ is —$NH_2$, and r is 1.

In a particular embodiment of the invention, S is a moiety of formula (S1) wherein $R^6$ is hydrogen, $R^7$ is hydrogen, $R^8$ is —NH—C(O)—$CH_3$, and r is 1.

In a particular embodiment of the invention, S is a moiety of formula (S1) wherein $R^6$ is —$NH_2$ or —NH—C(O)—$C_{1-7}$ alkyl, $R^7$ is hydrogen, $R^8$ is hydrogen, and r is 1.

In a particular embodiment of the invention, S is a moiety of formula (S1) wherein $R^6$ is —$NH_2$ or —NH—C(O)—$CH_3$, $R^7$ is hydrogen, $R^8$ is hydrogen, and r is 1.

In a particular embodiment of the invention, S is a moiety of formula (S1) wherein $R^6$ is —$NH_2$, $R^7$ is hydrogen, $R^8$ is hydrogen, and r is 1.

In a particular embodiment of the invention, S is a moiety of formula (S1) wherein $R^6$ is —NH—C(O)—$CH_3$, $R^7$ is hydrogen, $R^8$ is hydrogen, and r is 1.

One particular embodiment of the invention relates to a conjugate of formula (Ia)

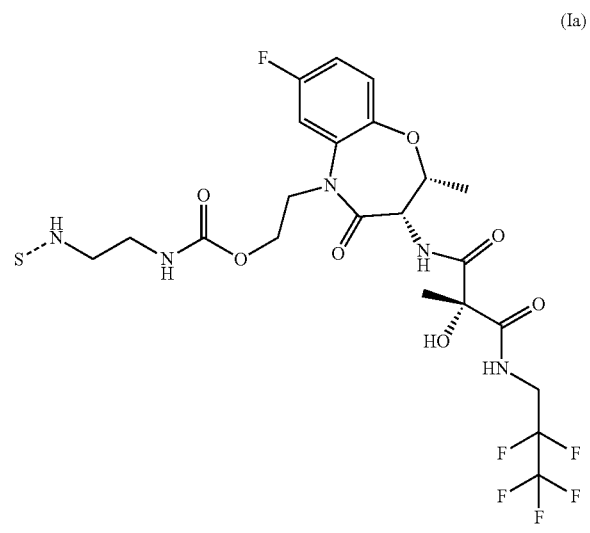

(Ia)

or a pharmaceutically acceptable salt thereof, wherein S is a peptidase-specific substrate as described herein.

One particular embodiment of the invention relates to conjugates of formula (Ib)

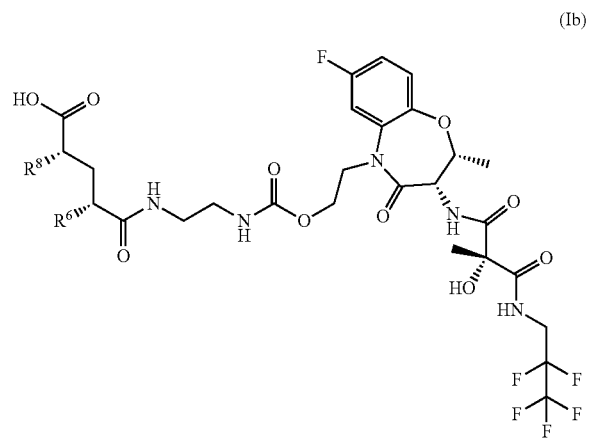

(Ib)

wherein one of $R^6$ or $R^8$ is —$NH_2$ or —NH—C(O)—$C_{1-7}$ alkyl and the other one of $R^6$ or $R^8$ is hydrogen.

In a particular embodiment of the invention, one of $R^6$ or $R^8$ is —$NH_2$ or —NH—C(O)—$CH_3$ and the other one of $R^6$ or $R^8$ is hydrogen.

In a particular embodiment of the invention, $R^6$ is —$NH_2$ or —NH—C(O)—$CH_3$ and $R^8$ is hydrogen.

In a particular embodiment of the invention, $R^8$ is —$NH_2$ or —NH—C(O)—$CH_3$ and $R^6$ is hydrogen.

In a particular embodiment of the invention, $R^6$ is —$NH_2$ and $R^8$ is hydrogen.

In a particular embodiment of the invention, $R^6$ is —NH—C(O)—$CH_3$ and $R^8$ is hydrogen.

In a particular embodiment of the invention, $R^8$ is —$NH_2$ and $R^6$ is hydrogen.

In a particular embodiment of the invention, $R^8$ is —NH—C(O)—$CH_3$ and $R^6$ is hydrogen.

In a particular embodiment of the invention, the conjugate of formula (I) is selected from the list of:
- (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;
- (S)-2-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;
- (S)-4-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;
- (S)-4-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;
- (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoic acid;

and pharmaceutically acceptable salts thereof.

Another embodiment of the invention relates a conjugate of formula (II)

H—L—A    (II)

or a pharmaceutically acceptable salt thereof, wherein A is a γ-secretase inhibitor as described herein, L is a linker as described herein and H is hydrogen.

One particular embodiment of the invention relates to a compound of formula (IIa)

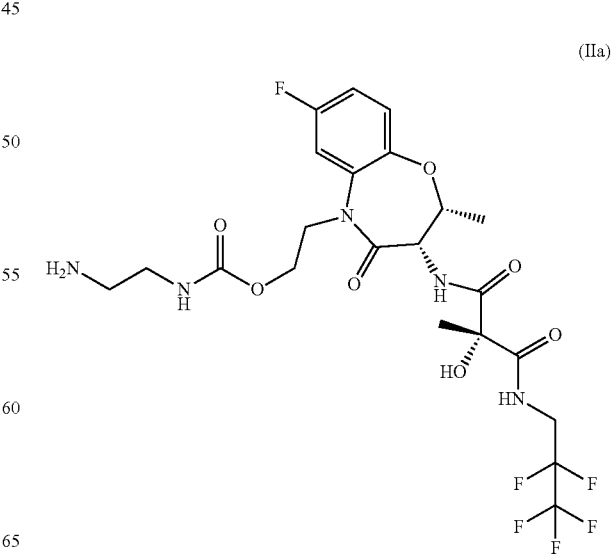

(IIa)

or a pharmaceutically acceptable salt thereof.

Compounds of formula (II) are suitable as intermediates for the manufacture of compounds of formula (I). Further Compounds of formula (II) as such exhibit high notch inhibiting activity.

Synthesis

Compounds of formula (A) can be prepared as described in WO 2006/061136 A2, e.g. according to the general synthetic schemes on pages 9 to 16. The compounds of formula (A) and their pharmaceutically acceptable salts can be prepared by methods known in the art, for example, by processes described below, which processes comprise a) reacting a compound of formula

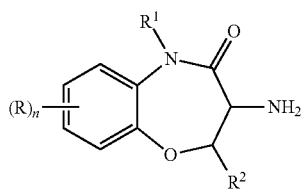

(A-II)

with a compound of formula

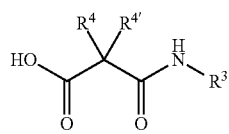

(A-III)

to a compound of formula

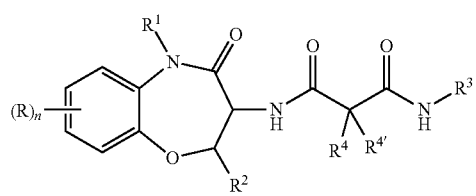

(A')

wherein R, R¹, R² R³ and R⁴/R⁴' and n are as described herein; or b) reacting a compound of formula

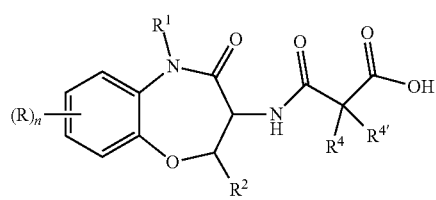

(A-IV)

with a compound of formula NH₂R³ (A-V)

to a compound of formula

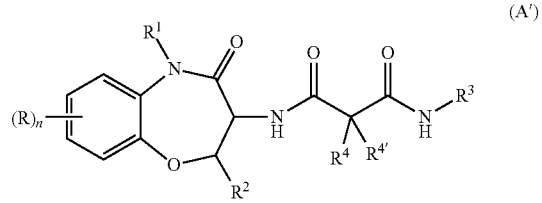

(A')

wherein R, R¹, R² R³ and R⁴/R⁴' and n are as described above; or c) reacting a compound of formula

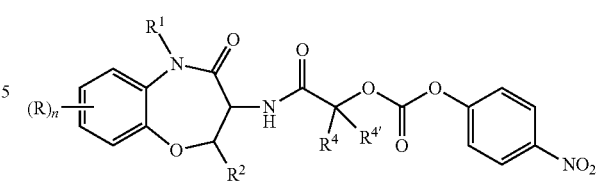

(A-VI)

with a compound of formula NH₂R³ (A-V)

to a compound of formula

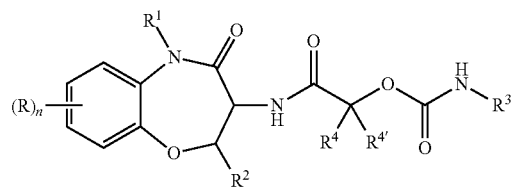

(A″)

wherein R, R¹, R² R³ and R⁴/R⁴' and n are as described above.

Alternatively, compounds of formula (A) can be prepared according to Scheme 1: Compounds of formula 8 can be prepared starting from the known chiral malonic half-ester 1. Standard peptide coupling followed by catalytic hydrogenation and saponification with lithium hydroxide afforded 4. The oxazepine 7 has been prepared from 5 via alkylation with benzyl 2-bromoethyl ether followed by Boc-removal with TFA. Peptide coupling of 4 with 7 and subsequent catalytic hydrogenation is affording 8 as a single isomer with (S)-configuration at the malonamide center.

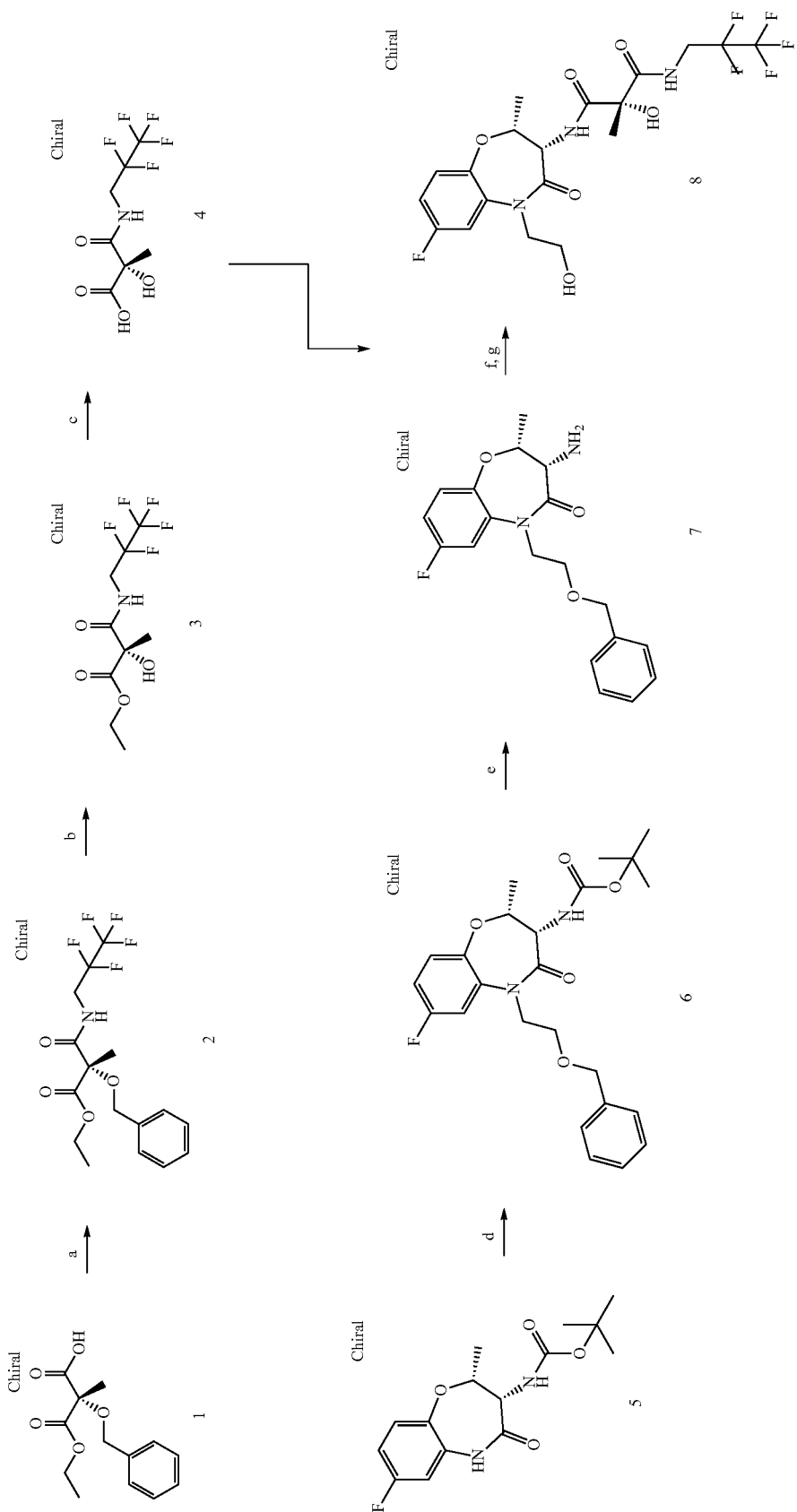

Conjugates of formula (I) can be prepared as described below in Scheme 2 and Scheme 3. The γ-secretase inhibitor 8 was reacted with bis(4-nitrophenyl)carbonate to give carbonate 9 in 90% yield, then the mono BOC protected ethylenediamine could be attached in 93% yield to give 10a. Reaction with N-BOC-gycinol in the presence of DMAP gave 10b in 77% yield. Deprotection with HCl in dioxane gave the linker-functionalized γ-secretase inhibitor 11a or 11b, allowing attachment of the N-protected and free α- and γ-glutamyl substrates.

The conjugate 13a with Ac-γ-Glu as moiety of formula (S) and Y equal NH was synthesized from carbamate 11a in two steps with Ac-Glu(OSU)-OBzl followed by hydrogenation of the benzylester (Scheme 2). The non-protected conjugate 13b (with H-γ-Glu) was synthesized in two steps with BOC-Glu-OtBu and EDCI coupling followed by HCl deprotection in total of 82% yield (Scheme 2). The conjugate 13c with Ac-γ-Glu as moiety of formula (S) and Y equal O was synthesized from carbonate 11c in two steps with Ac-Glu-OMe followed by lithium hydroxide hydrolysis of the methyl ester (Scheme 2).

The same amine building block 11a was used for the synthesis of the conjugates 15a (Ac-α-Glu) and 15b (H-α-Glu). EDCI coupling of amine 11a with Ac-Glu(OtBu)-OH in the presence of 1-hydroxy-7-azabenzotriazole gave amide 14a in quantitative yield. Ester deprotection with HCl in dioxane gave conjugate 15a in 81% yield. Conjugate 15b was synthesized the same way with BOC-Glu(OtBu)-OH coupling in quantitative yield followed by double deprotection to give 15b in 80% yield (Scheme 3).

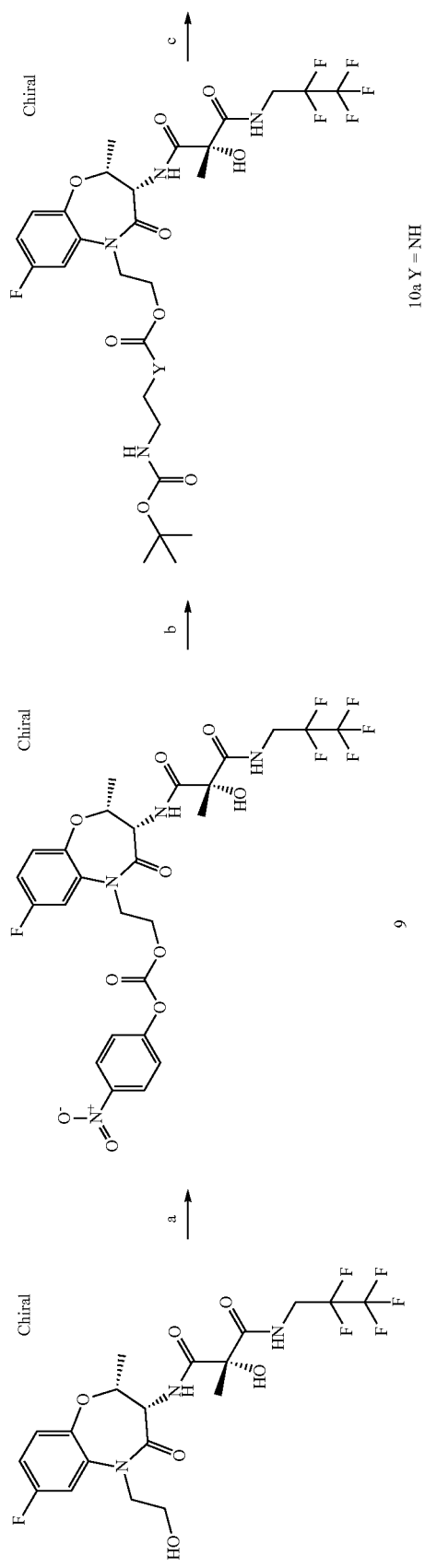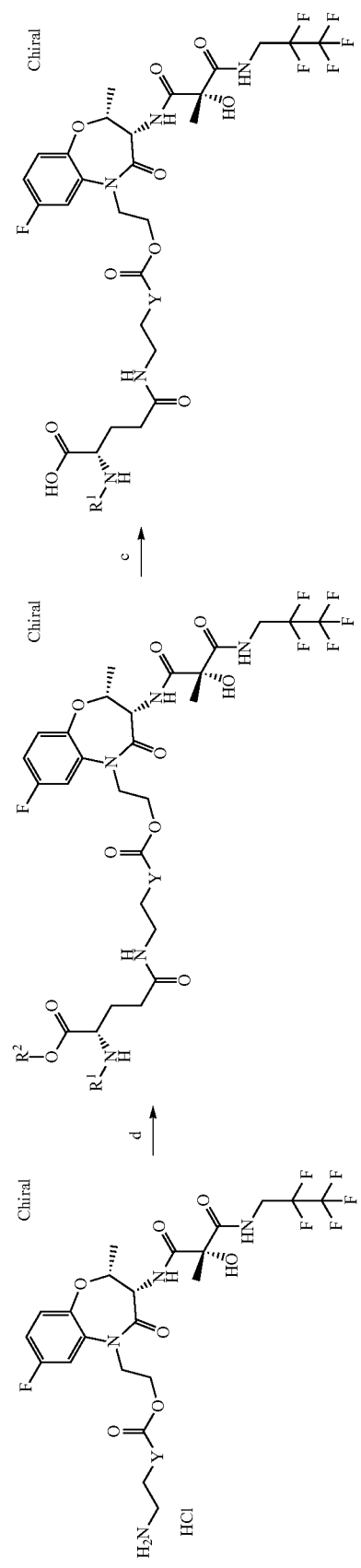

Scheme 2.

Synthesis of the amine-Secrl 11a and amine-O-Secrl 11b, Ac-γ-Glu-Secrl 13a, H-γ-Glu-γ-Glu-Secrl 13b and Ac-γ-Glu-O-Secrl 13c.
Reagents and conditions: (a) Bis(4-nitrophenyl)carbonate, i-Pr₂NEt in CH₂Cl₂, r.t., 90%; for 10a: N-BOC-ethylenediamine, Et₃N in CH₂Cl₂, 0° C. to r.t., (11a: 77%; 11b: 91%); (b) for 10a: N-BOC-ethylenediamine, Et₃N in CH₂Cl₂, 0° C. to r.t., 93%; for 10b: N-BOC-gycinol, Et₃N/DMAP in CH₂Cl₂, 0° C. to r.t., 77%; (c) 4M HCl in dioxane in CH₂Cl₂, 0° C. to r.t., (11a: 77%; 11b: 91%); (d) for 12a: Ac-Glu(OSU)-OBzl, Et₃N in DMF, 0° C. to r.t., 52%; for 12b: BOC-Glu-OtBu, 1-hydroxy-7-azabenzotriazole, Et₃N and EDCl in DMF, 0° C. to r.t., 83%; for 12c: BOC-Glu-OMe, 1-hydroxy-7-azabenzotriazole, Et₃N and EDCl in DMF, 0° C. to r.t., 82%; for 13a: H₂/Pd-C 10%, in dioxane and MeOH, r.t., 82%; for 13b: 4M HCl in dioxane in CH₂Cl₂, 0° C. to r.t., quantative; for 13c: 0.9 eq. aq. LiOH in THF, 0° C., 36%.

Scheme 3. Synthesis of the Ac-α-Glu-SecrI (15a) and H-α-Glu-SecrI (15b)
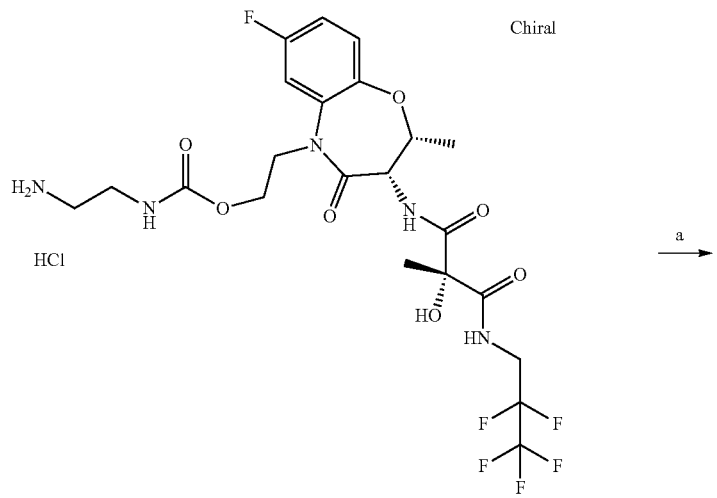
11a
a →
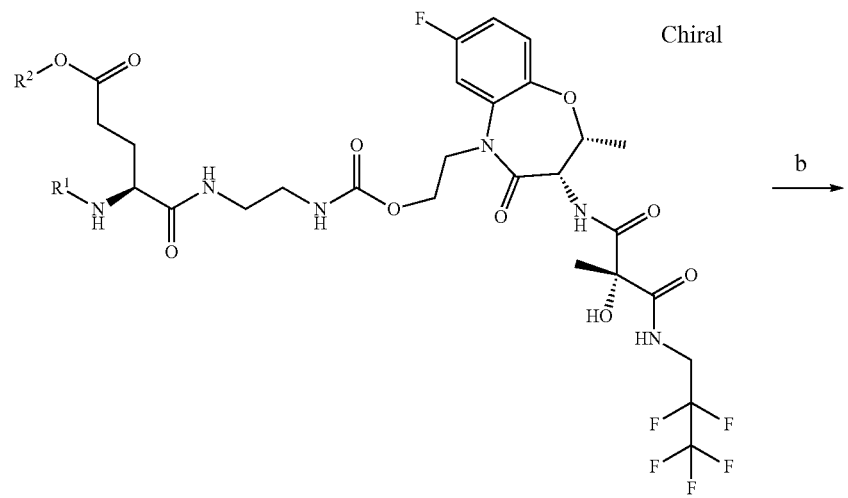
14a R[1] = Ac; R[2] = t-Bu
14b R[1] = t-Bu; R[2] = t-Bu
b →

-continued

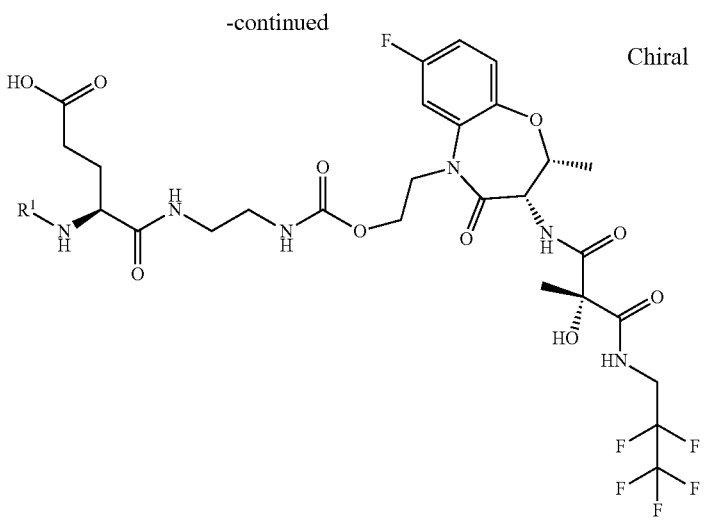

15a R¹ = Ac
15b R¹ = H•HCl

Reagents and conditions: (a) for 14a: Ac-Glu(OtBu)-OH, 1-hydroxy-7-azabenzotriazole, Et3N and EDCl in DMF, 0° C. to r.t., quantitative; for 14b: BOC-Glu(OtBu)-OH, 1-hydroxy-7-azabenzotriazole, Et3N and EDCl in DMF, 0° C. to r.t., quantitative; (b) 4M HCl in dioxane in CH2Cl2, 0° C. to r.t.; for 15a: 81%; for 15b: 80%.

The chemical structures and the enzymatic activities required for releasing active drugs are summarized in Scheme 4.

Scheme 4. Chemical structures and targeted enzymatic activities of the analogues of the γ-secretase inhibitor.

| | Y | S | releasing peptidase(s) |
|---|---|---|---|
| 8 | | | none |
| 11a | NH | H | none |
| 11b | O | H | none |
| 15b | NH | H-α-Glu- | APA |
| 15a | NH | Ac-α-Glu- | ACY1 and APA |
| 13b | NH | H-γ-Glu- | γ-GT / γ-GCT |
| 13a | NH | Ac-γ-Glu- | ACY1 and γ-GT / γ-GCT |
| 13c | O | Ac-γ-Glu- | ACY1 and γ-GT / γ-GCT |

The prodrugs are composed of three distinct parts: the active compound (γ-secretase inhibitor, SecrI), the linker (amino-ethyl-carbamate) and the targeting substrate for the releasing peptidases (arrow).

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C, Handbook of Pharmaceutical Excipients (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 µm filter, to remove impurities and contaminants.

Therapeutic Uses

As described above, the compounds of formula (I) and their pharmaceutically acceptable salts possess valuable pharmacological properties and have been found to be selective renal notch pathway inhibitors or γ-secretase inhibitors.

The compounds of the present invention can be used, either alone or in combination with other drugs, for the treatment or prevention of diseases caused by γ-secretase activity or activation of the Notch protein. These diseases include, but are not limited to renal diseases and tissue damage in the kidney, particularly acute kidney injury, chronic kidney disease, podocyte injury, glomerulosclerosis, tubulo-interstitial fibrosis, proteinuria, end-stage renal disease.

A particular embodiment of the invention also relates to a pharmaceutical composition comprising a compound of formula (I) as described herein and at least one pharmaceutically acceptable excipient.

A particular embodiment of the invention also relates to a compound of formula (I) as described herein for use as therapeutically active substances.

A particular embodiment of the invention also relates to a compound of formula (I) as described herein for use in the treatment or prevention of diseases which are related to γ-secretase activity or activation of the Notch protein.

A particular embodiment of the invention also relates to a compound of formula (I) as described herein for use in the treatment or prevention of renal diseases and tissue damage in the kidney, particularly of acute kidney injury, chronic kidney disease, podocyte injury, glomerulosclerosis, tubulo-interstitial fibrosis, proteinuria, end-stage renal disease.

In another embodiment, the invention relates to a method for the treatment or prevention of diseases which are related to γ-secretase activity or activation of the Notch protein, which method comprises administering a compound of formula (I) as described herein to a human being or animal.

In another embodiment, the invention relates to a method for the treatment or prevention of renal diseases and tissue damage in the kidney, particularly of acute kidney injury, chronic kidney disease, podocyte injury, glomerulosclerosis, tubulo-interstitial fibrosis, proteinuria, end-stage renal disease, which method comprises administering a compound of formula (I) as described herein to a human being or animal.

The invention also embraces the use of a compound of formula (I) as described herein for the treatment or prevention of diseases which are related to γ-secretase activity or activation of the Notch protein.

The invention also embraces the use of a compound of formula (I) as described herein for the treatment or prevention of renal diseases and tissue damage in the kidney, particularly of acute kidney injury, chronic kidney disease, podocyte injury, glomerulosclerosis, tubulo-interstitial fibrosis, proteinuria, end-stage renal disease.

The invention also relates to the use of a compound of formula (I) as described herein for the preparation of medicaments for the treatment or prevention of diseases which are related to γ-secretase activity or activation of the Notch protein.

The invention also relates to the use of a compound of formula (I) as described herein for the preparation of medicaments for the treatment or prevention of renal diseases and tissue damage in the kidney, particularly of acute kidney injury, chronic kidney disease, podocyte injury, glomerulosclerosis, tubulo-interstitial fibrosis, proteinuria, end-stage renal disease. Such medicaments comprise a compound of formula (I) as described above.

White: HEK293 cells; light grey: 215/F2 cells; dark grey: HK2 cells; black: EC219 cells Cpd added: 20 μM in PBS, 19 h incubation. SecrI (8) is stable when added to cells for 19 h; free SecrI (8) was never detected from any prodrug.

Figure 1A:
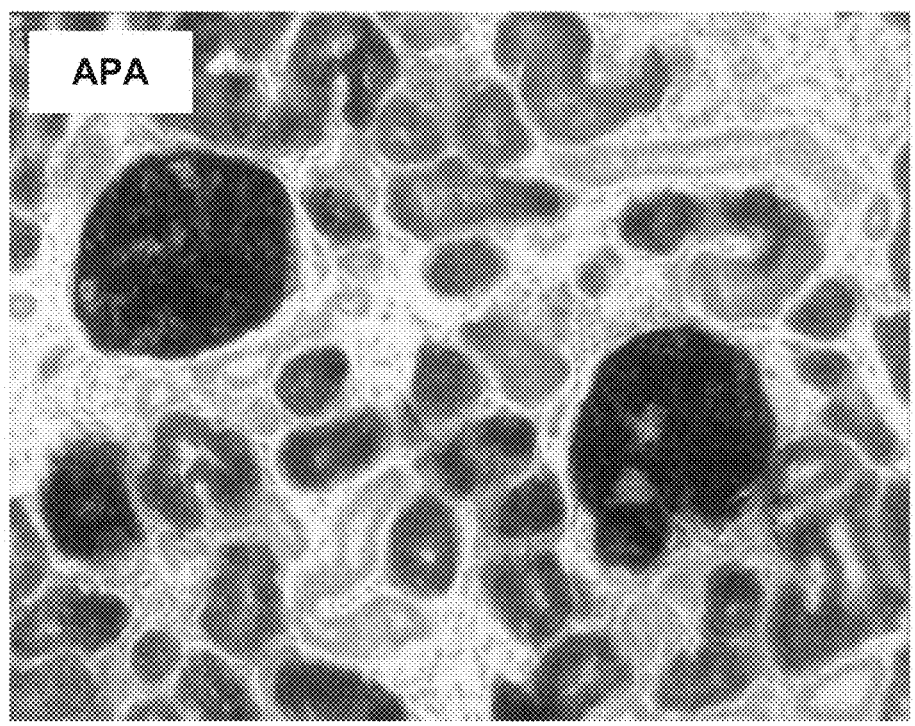
FIG. 1A. Histoenzymography of the enzymatic activities of APA in human diseased kidneys. Sections (7 µm) of frozen OCT-embedded human diseased kidneys were exposed at 37° C. to β-methoxynaphthylamide (β-NA) specific substrates of APA (α-Glu-βNA) and Fast Blue B, then the sections were counterstained with light hematoxylin reagent. Enzymatic activity is visualized as a red precipitate.
Figure 1B:
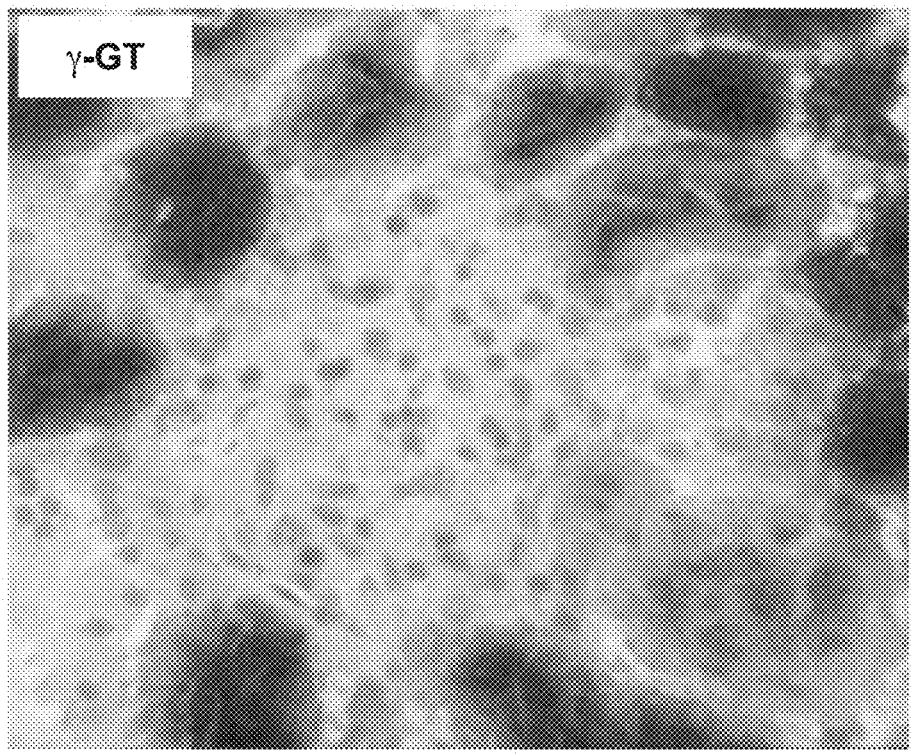
FIG. 1B. Histoenzymography of the enzymatic activities of γ-GT in human diseased kidneys. Sections (7 μm) of frozen OCT-embedded human diseased kidneys were exposed at 37° C. to β-methoxynaphthylamide (β-NA) specific substrates of γ-GT (γ-Glu-βNA) and Fast Blue B, then the sections were counterstained with light hematoxylin reagent. Enzymatic activity is visualized as a red precipitate.
Figure 2A:
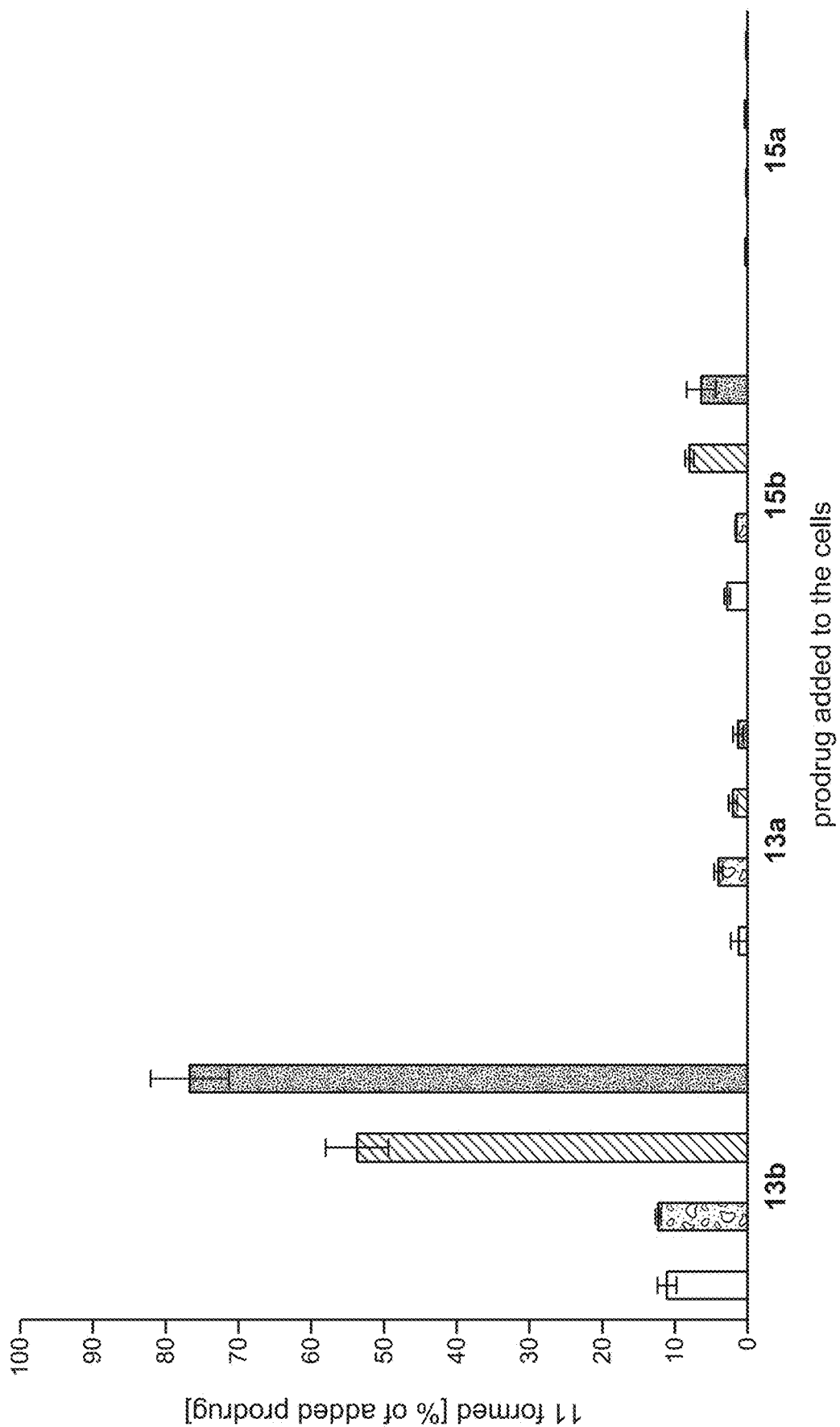
FIG. 2A. Extracellular release of amine-SecrI (11a) metabolites for α-Glu- and γ-Glu-secretase inhibitor prodrugs. The prodrugs were added to the cells for 19 h, then the supernatants were harvested and analyzed for SecrI (8), amine-SecrI (11a), the prodrugs 13a, 13b, 15a, 15b and (for 13a, 15a) also the correponding deacetylated metabolites.
Figure 2B:
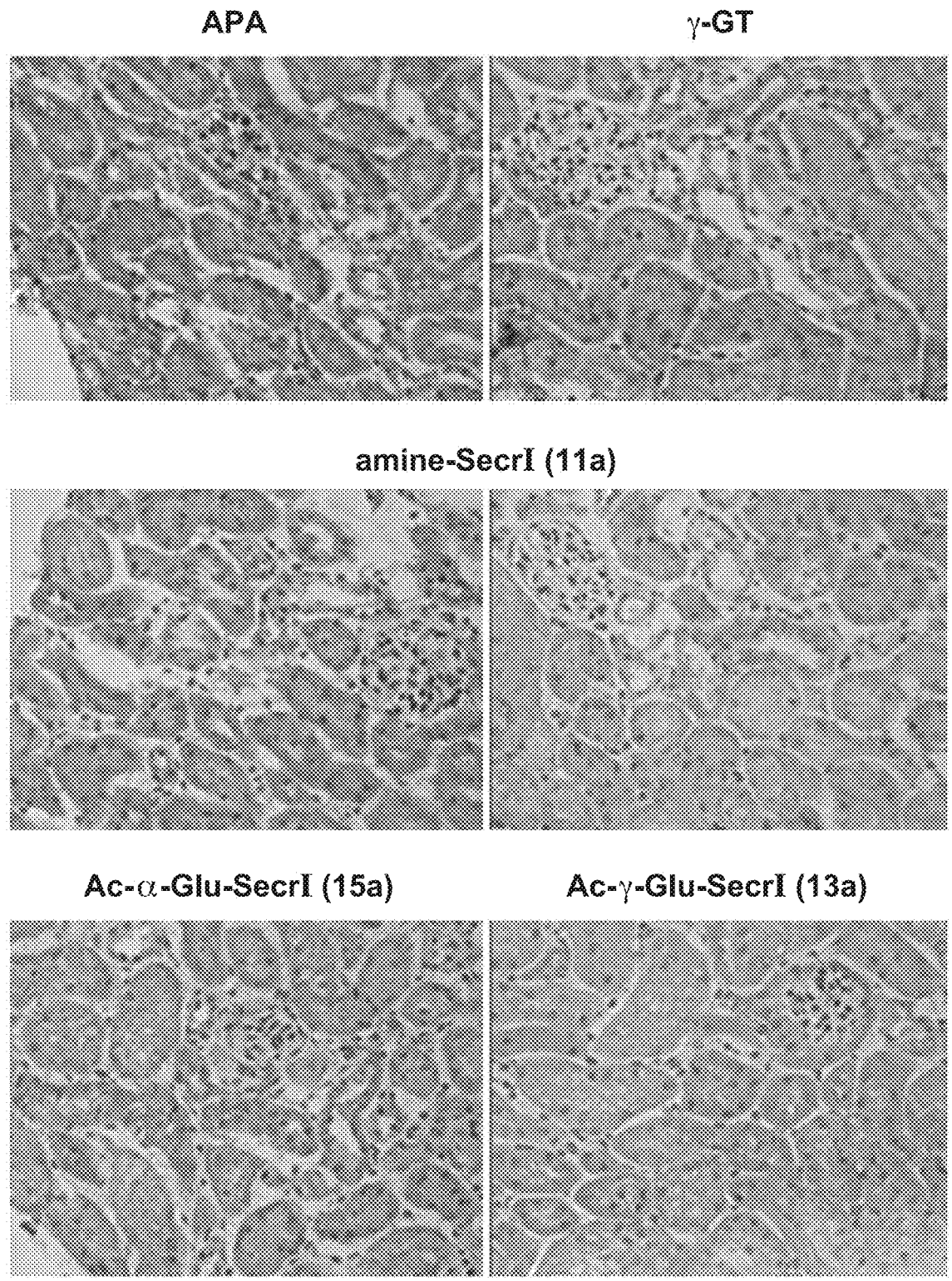

FIG. 2B. Selective inhibition of the enzymatic activities of APA and yGT by the γ-secretase analogues determined by histoenzymography in the kidneys of non diseased BALB/c mice.

Figure 3:
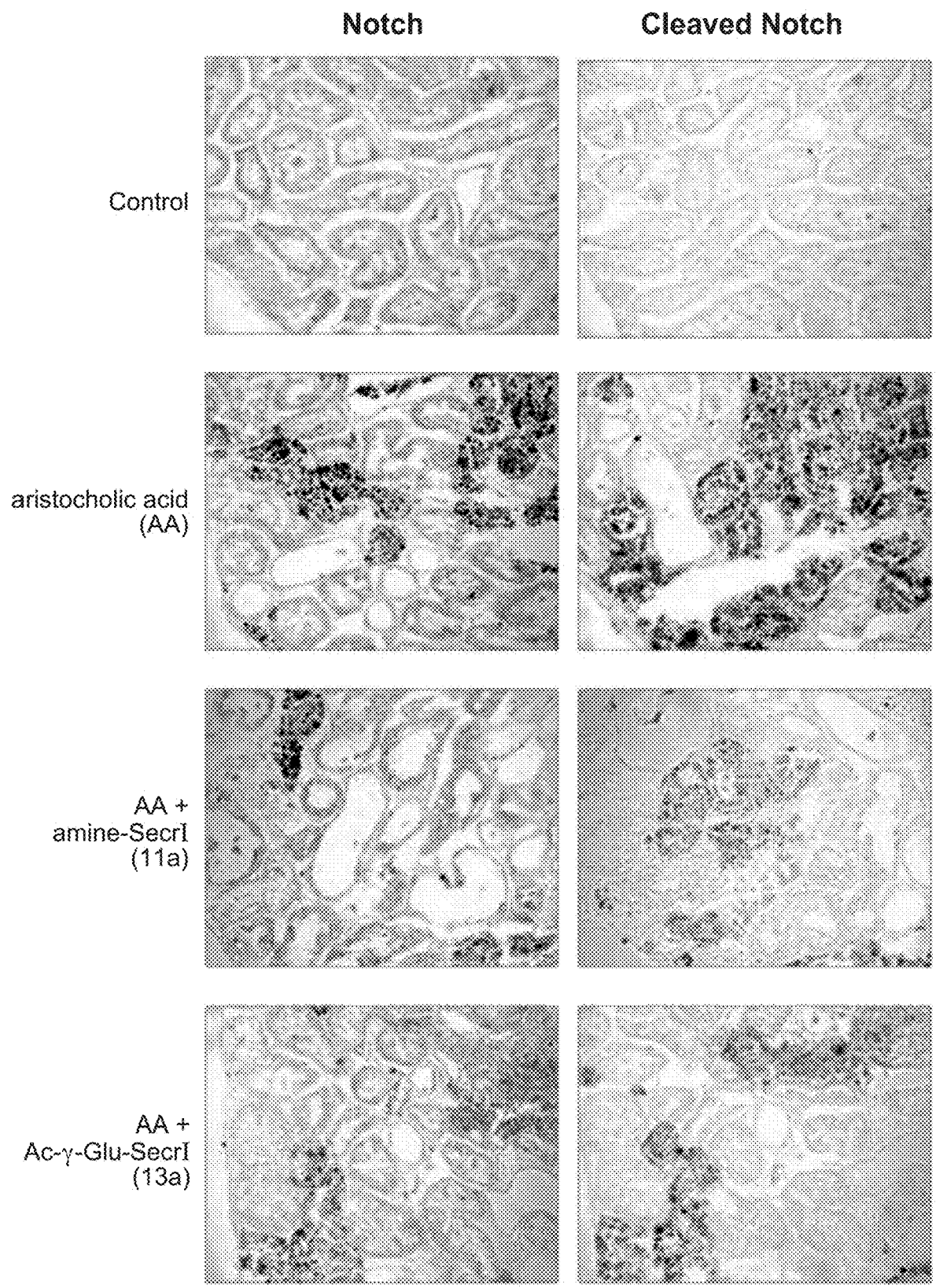

FIG. 3. Expression of Notch1 and active cleaved Notch1 determined by immuno-histochemistry in kidneys of mice exposed to aristolochic acid (AA) and treated either with the amine-SecrI (11a) or with Ac-γ-Glu-SecrI (13a).

Sections (7 μm) of snap-frozen kidneys were exposed to an anti-γ-secretase-cleaved Notch (cNotch) antibody, followed by the alkaline phosphatase fast-red chromogen staining. Immunostaining is visualized as dark precipitate.

EXAMPLES

The following examples 1-16 are provided for illustration of the invention. They should not be considered as limiting the scope of the invention, but merely as being representative thereof.

ABBREVIATIONS USED

Ac: acetyl
AA: aristolochic acid; 8-methoxy-6-nitrophenanthro[3,4-d][1,3]dioxole-5-carboxylic acid
APA: glutamyl aminopeptidase (EC 3.4.11.7)
γ-GT: γ-glutamyltranspeptidase (EC 2.3.2.2)
γ-GCT: γ-glutamylcyclotransferase (EC 2.3.2.4)
ACY1: N-acyl-L-amino-acid amidohydrolase (3.5.1.14)
AcOH: acetic acid
Ac-Glu(OSU)-OBzl: Acetyl-L-glutamic acid γ-N-hydroxysuccinimide ester α-benzyl ester
BOC: tert-butyloxycarbonyl
BOC-Glu(OtBu)-OH: N-Boc-L-glutamic acid γ-tert-butyl ester
n-BuLi: n-butyllithium
CH$_2$Cl$_2$: dichloromethane
DMAP: 4-dimethylaminopyridine
EDCI: N-(3-dimethylaminopropyl)-N'-ethylcarbodiimide hydrochloride
EtOAc: ethylacetate
EtOH: ethanol
Et$_2$O: diethylether
Et$_3$N: triethylamine
HOBT: 1-hydroxybenzotriazole hydrate
MeOH: methanol
i-Pr$_2$NEt: N-ethyl diisopropylamine
TFA: trifluoroacetic acid
THF: tetrahydrofuran
SecrI: γ-secretase inhibitor
BQL: below quantifiable limit.

General Information and Analytical Compound Characterization

Reactions were carried out under an atmosphere of argon. Solvents and reagents were obtained from commercial sources and were used as received. All reactions were followed by TLC (TLC plates F254, Merck). Proton and carbon NMR spectra were obtained on a Bruker 300, 400 or 600 MHz instrument. The respective carbon NMR spectra were 150 MHz. The chemical shifts (δ in ppm) are reported relative to tetramethylsilane as internal standard. NMR abbreviations are as follows: s, singlet; d, doublet; t, triplet; q, quadruplet; m, multiplet; br, broadened. Purity was analyzed by $^1$H NMR. In the $^1$H NMR spectra, the acidic protons of the HCl salt and the acid (COOH) were not seen. LC-MS were recorded on Waters UPLC-MS Systems equipped with Waters Acquity, a CTC PAL auto sampler and a Waters SQD single quadrupole mass spectrometer. The separation was achieved on a Zorbax Eclipse Plus C18 1.7 μm 2.1*30 mm column at 50° C.; A=0.01% formic acid in Water; B=acetonitrile at flow 1. gradient: 0 min 3% B, 0.2 min 3% B, 2 min 97% B, 1.7 min 97% B, 2.0 min 97% B. The injection volume was 2 μL. LC-MS high resolution spectra were recorded with an Agilent LC-system consisting of Agilent 1290 high pressure gradient system, a CTC PAL auto sampler and an Agilent 6520 QTOF. The separation was achieved on a Zorbax Eclipse Plus C18 1.7 μm 2.1*50 mm column at 55° C.; A=0.01% formic acid in Water; B=0.01% formic acid in acetonitrile at flow 1 mL/min. gradient: 0 min 5% B, 0.3 min 5% B, 4.5 min 99% B 5 min 99% B. The injection volume was 2 μL. Ionization was performed in Agilents Multimode source. The mass spectrometer was run in "2 GHz extended dynamic range" mode, resulting in a resolution of about 10 000 at m/z=922. Mass accuracy was ensured by internal drift correction.

Example 1

γ-Secretase Inhibitor (SecrI) 8

N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(S)-hydroxy-2-methyl-N'-(2,2,3,3,3-pentafluoro-propyl)-malonamide

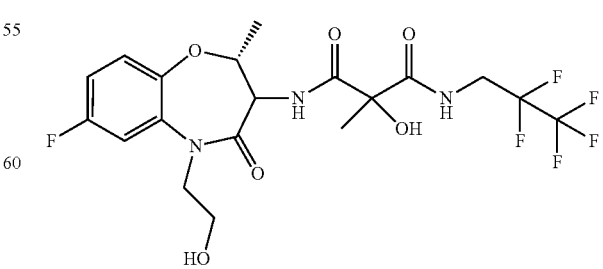

The title compound was prepared as described in WO 2006/061136 A2 for Example 70a (p. 95-97).

Step a) N-((6R,7S)-9-Allyl-2-fluoro-6-methyl-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide To a solution of 0.06 g (0.31 mmol) (6R,7S)-9-allyl-7-amino-2-fluoro-6-methyl-6,7-dihydro-9H-5-oxa-9-aza-benzocyclohepten-8-one in 5 ml tetrahydrofurane were added 0.07 g (0.31 mmol) 2-hydroxy-2-methyl-N-(2,2,3,3,3-pentafluoro-propyl)-malonamic acid, 0.04 g (0.31 mmol) 1-hydroxybenzotriazole hydrate, 0.06 g (0.31 mmol) N-(3-dimethylaminopropyl)-N'-ethyl-carbodiimid-hydrochlorid and 0.1 ml (0.62 mmol) diisopropylethylamine. After stirring at room temperature over night the mixture was added to 1N aqueous hydrochloric acid. Extraction with dichloromethane, followed by washing with saturated aqueous sodium bicarbonate solution and drying with sodium sulfate, and chromatography on silicagel with ethylacetate/heptane yielded the title compound as white solid, MS m/e (%): 498.5 (M+H+, 100).

Step b) N-[(6R,7S)-2-Fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide A solution of 1.30 g (3 mmol) (6R,7S)-9-allyl-7-amino-2-fluoro-6-methyl-6,7-dihydro-9H-5-oxa-9-aza-benzocyclohepten-8-one in 60 ml dichloromethane was treated with ozone at −75° C. for 60 minutes. Methyl sulfide, 0.81 g (13 mmol), was added and the solution was stirred for 16 hours at room temperature. The solvent was distilled off under vacuum and the residue was chromatographed in silicagel with n-heptane/ethylacetate 100:0 to 0:100 to yield 1.07 g (82%) N-[(6R,7S)-2-fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide, MS m/e (%): 500.3 (M+H+, 100).

Step c) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide 1.00 g (2.0 mmol N-[(6R,7S)-2-Fluoro-6-methyl-8-oxo-9-(2-oxo-ethyl)-6,7,8,9-tetrahydro-5-oxa-9-aza-benzocyclohepten-7-yl]-2-hydroxy-2-methyl-N-(2,2,3,3,3-pentafluoro-propyl)-malonamide in 30 ml tetrahydrofurane were reduced with 0.09 g (2.0 mmol) sodium borohydride. Chromatography on silicagel with ethylacetate/heptane 0:100 to 100:0 yielded 0.33 g (34%) N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide, MS m/e (%): 502.0 (M+H+, 100).

Step d) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-(S)-hydroxy-2-methyl-N-(2,2,3,3,3-pentafluoro-propyl)-malonamide 0.31 g (1.0 mmol) N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N-(2,2,3,3,3-pentafluoro-propyl)-malonamide epimers were separated by chromatography on Chiralpak AD with isopropanol/heptane 15:85 to yield 0.11 g N-[(6R,7S)-2-fluoro-9-(2-hydroxy-ethyl)-6-methyl-8-oxo-6,7,8,9-tetrahydro-5-oxa-9-aza-benzocyclohepten-7-yl]-2-(S)-hydroxy-2-methyl-N-(2,2,3,3,3-pentafluoro-propyl)-malonamide MS m/e (%): 502.3 (M+H+, 100).

Example 2

γ-Secretase Inhibitor (SecrI) 8

(2S)—N-[(2R,3S)-7-Fluoro-5-(2-hydroxyethyl)-2-methyl-4-oxo-2,3-dihydro-1,5-benzoxazepin-3-yl]-2-hydroxy-2-methyl-N'-(2,2,3,3,3-pentafluoropropyl)propanediamide

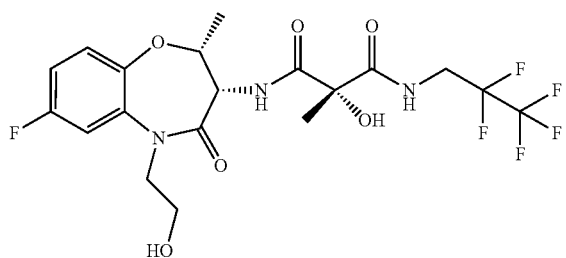 [SMILES: C[C@H]1Oc2ccc(F)cc2N(CCO)C(=O)[C@H]1NC(=O)[C@@](C)(O)C(=O)NCC(F)(F)C(F)(F)F]

Step a) Ethyl (2S)-2-benzyloxy-2-methyl-3-oxo-3-(2,2,3,3,3-pentafluoropropylamino)propanoate (2)

A mixture of (2S)-2-benzyloxy-3-ethoxy-2-methyl-3-oxo-propanoic acidl (1) (1.2 g, 4.75 mmol), 2,2,3,3,3-pentafluoropropylamine (722 mg, 4.75 mmol), HOBt (654 mg, 4.75 mmol), EDCI (928 mg, 4.75 mmol) and i-Pr$_2$NEt (2.1 ml, 11.9 mmol) in THF (20 mL) was stirred for 18 h at ambient temperature. Volatiles were evaporated off in vacuo. Resulting crude material was purified by flash chromatography (50 g Silica-cartridge, n-heptane/EtOAc 0-30%) to afford the title compound (1.08 g, 59.4%) as colorless liquid. $^1$H NMR (300 MHz, CDCl$_3$): δ=7.37 (m, 5H), 7.26 (m, 1H), 4.60 (d, J=36 Hz, 1H), 4.42 (d, J=36 Hz, 1H), 4.25 (q, 24 Hz, 2H), 4.25 (m, 2H), 1.75 (s, 3H), 1.28 (t, J=24 Hz, 3H). LC-MS: 382.3 (M−H)−.

Step b) Ethyl (2S)-2-hydroxy-2-methyl-3-oxo-3-(2,2,3,3,3-pentafluoropropylamino)propanoate (3)

Under Argon and stirring, ethyl (2S)-2-benzyloxy-2-methyl-3-oxo-3-(2,2,3,3,3-pentafluoropropylamino)propanoate (2) (1.0 g, 2.61 mmol) was dissolved in MeOH (70 mL) with aq. HCl (37%, 3 drops) and Pd—C 10% (278 mg, 0.26 mmol) was added. After evacuation and replacing with H$_2$ (5 times) the mixture was hydrogenated for 18 h, then filtered, washed with MeOH and evaporated to afford the title compound (766 mg, >99%) as white solid. $^1$H NMR (300 MHz, CDCl$_3$): δ=4.32 (m, 2H), 4.10 (s, 1H), 3.97 (m, 2H), 1.67 (m, 3H), 1.33 (t, J=24 Hz, 3H). LC-MS: 294.0 (M+H)+. Melting-point 41-42° C.

Step c) (2S)-2-Hydroxy-2-methyl-3-oxo-3-(2,2,3,3,3-pentafluoropropylamino)propanoic acid (4)

A mixture of ethyl (2S)-2-hydroxy-2-methyl-3-oxo-3-(2,2,3,3,3-pentafluoropropylamino) propanoate (3) (716 mg, 2.44 mmol) and LiOH (239 mg, 9.77 mmol) in THF (10 mL) and water (2 mL) was stirred for 18 h at ambient temperature. The mixture was diluted with water and extracted with EtOAc. The aqueous phase was acidified with aq. HCl (37%) to pH 0 and extracted twice with EtOAc. The combined organic layers were washed with brine, dried over MgSO$_4$ and evaporated to dryness affording the title compound (537 mg, 83%) as white solid. $^1$H NMR (300 MHz, CDCl$_3$): δ=7.42 (s, broad, 1H), 4.40 (s, broad, 1H), 4.05 (m, 2H) 1.72 (s, 3H). LC-MS: 264.3 (M−H)$^−$. Melting-point 67-69° C.

Step d) tert-Butyl N-[(2R,3S)-5-(2-benzyloxyethyl)-7-fluoro-2-methyl-4-oxo-2,3-dihydro-1,5-benzoxazepin-3-yl]carbamate (6)

To a solution of tert-butyl N-[(2R,3S)-7-fluoro-2-methyl-4-oxo-3,5-dihydro-2H-1,5-benzoxazepin-3-yl]carbamate (500 mg, 1.61 mmol) in DMF (30 mL) was added sodium hydride (60% in mineral oil, 97 mg. 2.42 mmol) at room temperature under nitrogen atmosphere. The resulting mixture was stirred for 30 min, then benzyl 2-bromoethyl ether (107 mg, 0.48 mmol) was added and stirring was continued for further 18 h. The reaction mixture was quenched with water and extracted twice with EtOAc, the combined organic layers were washed with aq. citric acid and brine, dried over MgSO$_4$ and evaporated to dryness. Resulting crude material was purified by flash chromatography (20 g Silica-cartridge, n-heptane/EtOAc 0-20%) to afford the title compound (577 mg, 81%) as yellow oil. $^1$H NMR (300 MHz, CDCl$_3$): δ=7.27 (m, 6H), 7.09 (m, 1H), 6.88 (m, 1H), 5.50 (br. d, 1H), 4.72 (m, 2H), 4.51 (s, 2H), 3.99 (m, 2H), 3.78 (m, 1H), 3.63 (m, 1H), 1.41 (d, J=20 Hz, 9H), 1.35 d, J=21 Hz, 3H). LC-MS: 445.4 (M+H)$^+$.

Step e) (2R,3S)-3-Amino-5-(2-benzyloxyethyl)-7-fluoro-2-methyl-2,3-dihydro-1,5-benzoxazepin-4-one (7)

A mixture of tert-butyl N-[(2R,3S)-5-(2-benzyloxyethyl)-7-fluoro-2-methyl-4-oxo-2,3-dihydro-1,5-benzoxazepin-3-yl]carbamate (6) (540 mg, 1.22 mmol) and TFA (2.34 mL, 30.4 mmol) in CH$_2$Cl$_2$ (30 mL) was stirred for 18 h at ambient temperature under nitrogen atmosphere. The mixture was made basic with an excess of sat. aq. NaHCO$_3$, then diluted with water and extracted twice with EtOAc. The combined organic layers were dried with MgSO$_4$ and evaporated to dryness, affording the title compound (411 mg, 98%) as yellow oil. $^1$H NMR (300 MHz, CDCl$_3$): δ=7.27 (m, 6H), 7.08 (m, 1H), 6.88 (m, 1H), 4.54 (m, 3H), 4.07 (m, 1H), 3.85 (m, 3H), 3.67 (m, 1H),1.35 (d, J=22 Hz, 3H). LC-MS: 345.0 (M+H)$^+$.

Step f) (2S)—N-[(2R,3S)-7-Fluoro-5-(2-hydroxyethyl)-2-methyl-4-oxo-2,3-dihydro-1,5-benzoxazepin-3-yl]-2-hydroxy-2-methyl-N'-(2,2,3,3,3-pentafluoropropyl)propanediamide (8)

(2R,3S)-3-Amino-5-(2-benzyloxyethyl)-7-fluoro-2-methyl-2,3-dihydro-1,5-benzoxazepin-4-one (7) (207 mg, 0.60 mmol), (2S)-2-hydroxy-2-methyl-3-oxo-3-(2,2,3,3,3-pentafluoropropylamino)propanoic acid (4) (191 mg, 0.72 mmol), HOBt (91.2 mg, 0.66 mmol), EDCI (141 mg, 0.72 mmol) and i-Pr$_2$NEt (263 μL, 1.50 mmol) were dissolved in THF (10 mL) and stirred for 60 h at ambient temperature under nitrogen atmosphere. After evaporation to dryness, the crude material was purified by flash chromatography (20 g Silica-cartridge, n-heptane/EtOAc 0-30%), affording (2S)—N-[(2R,3S)-5-(2-benzyloxyethyl)-7-fluoro-2-methyl-4-oxo-2,3-dihydro-1,5-benzoxazepin-3-yl]-2-hydroxy-2-methyl-N'-(2,2,3,3,3-pentafluoropropyl)propanediamide (8a) (218 mg, 61%) as colorless, viscous oil. LC-MS: 592.3 (M+H)$^+$.

(2S)—N-[(2R,3S)-5-(2-Benzyloxyethyl)-7-fluoro-2-methyl-4-oxo-2,3-dihydro-1,5-benzoxazepin-3-yl]-2-hydroxy-2-methyl-N'-(2,2,3,3,3-pentafluoropropyl)propanediamide (8a) (209 mg, 0.35 mmol) was dissolved in MeOH (20 mL) with aq. HCl (37%, 2 drops) and Pd—C 10% (38 mg, 0.35 mmol) was added. After evacuation and replacing with H$_2$ (5 times) the mixture was hydrogenated for 18 h, then filtered, washed with MeOH and evaporated to afford the title compound (182 mg, >99%) as white foam. HPLC: tR 2.37 min, 99.3% (265 nm); tR 2.37 min, 99.3% (220 nm). $^1$HNMR (600 MHz, DMSO-d6): δ=8.56 (t, J=6.50 Hz, 1H), 7.84 (d, J=6.75 Hz, 1H), 7.57 (dd, J=3.02, 9.87 Hz, 1H), 7.27 (dd, J=5.64, 8.86 Hz, 1H), 7.13 (dt, J=3.02, 8.46 Hz, 1H), 6.74 (s, 1H), 5.00 (br s, 1H), 4.58-4.69 (m, 2H), 3.83-3.97 (m, 3H), 3.76 (ddd, J=5.69, 8.16, 13.95 Hz, 1H), 3.65 (ddd, J=5.19, 8.11, 11.08 Hz, 1H), 3.43-3.49 (m, 1H), 1.40 (s, 3H), 1.19 (d, J=6.04 Hz, 3H). $^{13}$C NMR (151 MHz, DMSO-d6): δ=171.8, 169.9, 167.4, 159.6, 158.0, 145.8, 145.8, 137.4, 137.3, 123.6, 123.5, 113.8, 113.7, 111.5, 111.3, 82.3, 76.5, 57.9, 51.5, 50.9, 38.0, 23.4, 15.5. LC-MS: 500.1 (M−H)$^+$. HRMS (C$_{19}$H$_{21}$F$_6$N$_3$O$_6$): calcd. 501.1335[M]; found 501.1345.

Example 3

Amine-γ-Secretase Inhibitor (Amine-SecrI) 11a 2-((2R,3S)-7-Fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 2-aminoethylcarbamate hydrochloride

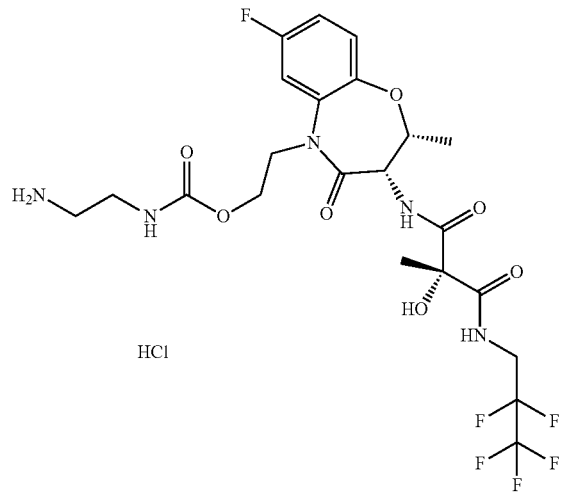 [SMILES: C[C@H]1Oc2ccc(F)cc2N(CCOC(=O)NCCN)C(=O)[C@H]1NC(=O)[C@@](C)(O)C(=O)NCC(F)(F)C(F)(F)F ; Cl]

Step a) 2-((2R,3S)-7-Fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 4-nitrophenyl carbonate (9)

To a solution of (S)—N-[(6R,7S)-2-fluoro-9-(2-hydroxyethyl)-6-methyl-8-oxo-6,7,8,9-tetrahydro-5-oxa-9-aza-benzocycloheptan-7-yl]-2-hydroxy-2-methyl-N'-(2,2,3,3,3-pentafluoro-propyl)-malonamide (8) (1 g, 1.99 mmol) in CH$_2$Cl$_2$ (75 mL) were added i-Pr2NEt (2.08 mL, 11.97 mmol) and bis(4-nitrophenyl)carbonate (1.82 g, 5.98 mmol), and the resulting clear yellow solution was stirred for 12 h at 25° C. under argon atmosphere. Reaction mixture was poured in to aq. 10% KHSO$_4$ (40 mL). Organic layer was separated, and the aq. layer was re-extracted with CH$_2$Cl$_2$ (2×40 mL). Combined organic layer was washed with aq. sat. NaHCO$_3$ (2×30 mL) and brine (30 mL), dried over anhydrous Na$_2$SO$_4$, filtered, and evaporated off in vacuo. Resulting crude material was purified by column chromatography over normal silica gel (2-8% EtOAc/n-hexane) to afford the title compound (1.2 g, 90%) as white solid. $^1$H NMR (300 MHz, DMSO-d6): δ=7.17 (ddd, J=8.5, 3.2 Hz, 1H), 8.27-8.37 (m, 2H), 7.84 (d, J=6.7 Hz, 1H), 7.42-7.52 (m, 3H), 7.32 (dd, J=8.9, 5.7 Hz, 1H), 7.17 (td, J=8.5, 3.2 Hz, 1H), 6.73 (s, 1H), 4.68-4.74 (m, 1H), 4.62 (dd, J=6.3 Hz, 1H), 4.42-4.56 (m, 2H), 4.20-4.32 (m, 1H), 3.95-4.06 (m, 1H), 3.78-3.94 (m, 2H), 3.29 (s, 3H), 1.39 (s, 3H), 1.21 (d, J=6.3 Hz, 3H). LC-MS: 667.2 (M+H)$^+$.

Step b) tert-Butyl N-[2-[2-[(2R,3S)-7-fluoro-3-[[(2S)-2-hydroxy-2-methyl-3-oxo-3-(2,2,3,3,3-pentafluoropropylamino)propanoyl]amino]-2-methyl-4-oxo-2,3-dihydro-1,5-benzoxazepin-5-yl]ethoxycarbonylamino]ethyl]carbamate (10a)

To a solution of 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 4-nitrophenyl carbonate (9) (1200 mg, 1.80 mmol) in CH$_2$Cl$_2$ (15 mL) at 0° C. under argon atmosphere were added drop wise a solution of N-BOC-ethylenediamine (317 mg, 1.98 mmol) in CH$_2$Cl$_2$ (9 mL) and Et$_3$N (1.05 mL, 1.89 mmol). Resultant reaction mixture was stirred at 0° C. for 1 h followed by another 12 h at 25° C. Reaction mixture was poured in to aq. 10% KHSO$_4$ (10 mL). Organic layer was separated, and the aq. layer was re-extracted with EtOAc (2×20 mL). Combined organic layer was dried over anhydrous Na$_2$SO$_4$, filtered, and evaporated off in vacuo. Resulting crude material was purified by flash chromatography (50 g Si-Amine, Cilicycle-cartridge, EtOAc/n-heptane 1:1 to 2:1) to afford the title compound (1.15 g, 93%) as white powder. $^1$H NMR (300 MHz, DMSO-d6): δ=8.56 (t, J=6.9 Hz, 1H), 7.82 (d, J=6.1 Hz, 1H), 7.40 (dd, J=9.7, 2.6 Hz, 1H), 7.28 (dd, J=9.0, 5.6 Hz, 1H), 7.15 (td, J=8.3, 2.4 Hz, 1H), 7.02 (br. s., 1H), 6.74 (s, 2H), 4.51-4.73 (m, 2H), 4.14 (d, J=19.8 Hz, 2H), 4.06 (d, J=4.6 Hz, 2H), 3.77-3.98 (m, 3H), 3.29 (s, 3H), 2.93 (br. s., 3H), 1.39 (s, 3H), 1.36 (s, 9H), 1.20 ppm (d, J=5.9 Hz, 3H). LC-MS: 688.2 (M+H)$^+$.

Step c) 2-((2R,3S)-7-Fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 2-aminoethylcarbamate hydrochloride (11a)

To a solution of tert-butyl N-[2-[2-[(2R,3S)-7-fluoro-3-[[(2S)-2-hydroxy-2-methyl-3-oxo-3-(2,2,3,3,3-pentafluoropropylamino)propanoyl]amino]-2-methyl-4-oxo-2,3-dihydro-1,5-benzoxazepin-5-yl]ethoxycarbonylamino]ethyl]carbamate (10a) (1.15 g, 1.67 mmol) in CH$_2$Cl$_2$ (5.7 mL) at 0° C. was added drop wise a solution of 4M HCl in dioxane (4.2 mL). Reaction mixture was stirred for 1.75 h at 25° C. Volatilities were evaporated off in vacuo. Resulting crude material was triturated with CH$_2$Cl$_2$/Et$_2$O to yield the title compound (997 mg, 96%) as off-white powder. HPLC: tR 1.67 min, 99.1% (265 nm); tR 1.67 min, 98.0% (220 nm). $^1$H NMR (600 MHz, DMSO-d6): δ=8.56 (t, J=6.55 Hz, 1H), 7.70-8.01 (m, 4H), 7.42 (dd, J=2.87, 9.62 Hz, 1H), 7.29 (dd, J=5.64, 8.87 Hz, 1H), 7.21 (t, J=5.74 Hz, 1H), 7.16 (dt, J=3.02, 8.46 Hz, 1H), 6.88 (br s, 1H), 6.74 (s, 1H), 4.64-4.68 (m, 1H), 4.57-4.64 (m, 1H), 4.24-4.52 (m, 1H), 4.13-4.23 (m, 1H), 4.05-4.12 (m, 2H), 3.79-3.99 (m, 3H), 3.17 (q, J=6.28 Hz, 2H), 2.86-3.12 (m, 1H), 2.74-2.86 (m, 2H), 2.62-2.74 (m, 1H), 1.39 (s, 3H), 1.21 (d, J=6.25 Hz, 3H). 13C NMR (151 MHz, DMSO-d6): δ=172.3, 170.4, 168.1, 160.1, 158.5, 156.4, 146.5, 146.5, 136.9, 136.8, 124.3, 124.2, 120.0, 114.7, 114.5, 113.6, 113.4, 111.5, 111.3, 82.7, 76.9, 61.3, 51.8, 47.0, 39.1, 38.7, 38.5, 38.4, 24.0, 15.9. LC-MS: 586.17 (M−H)$^−$. HRMS (C$_{22}$H$_{27}$F$_6$N$_5$O$_7$): calcd. 587.1815[M]; found 587.1841.

Example 4

Ac-γ-Glu-Prodrug (Ac-γ-Glu-SecrI) 13a (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid

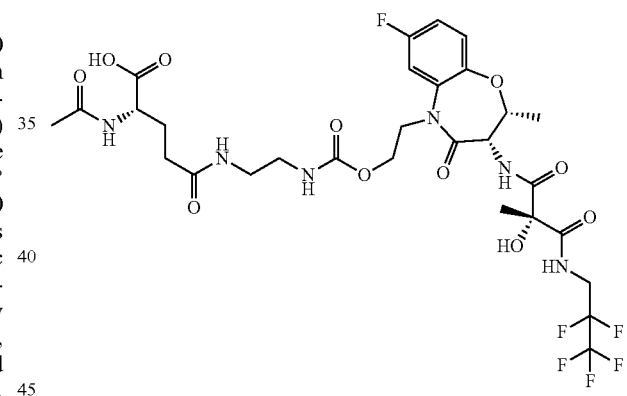

Step a) (S)-Benzyl 2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (12a)

To a nearly colorless solution of 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 2-aminoethylcarbamate hydrochloride (11a) (225 mg, 360 μmol) and Ac-Glu(OSU)-OBzl (149 mg, 396 μmol) in DMF (3.99 mL) under Argon at 0° C. was added 1/3 of a solution of Et$_3$N (40.1 mg, 55.2 μl, 396 μmol) in DMF (2.40 mL) dropwise over 15 min. (sol. became light yellow). After 15 min the second third amount was added over 15 min and after 15 min the last third over 15 min. The reaction was allowed to warm to rt over night. There was still starting amine detected in LC/MS. The reaction was cooled to 0° C. again, Et3N (40.1 mg, 55.2 µl, 396 µmol) in DMF (1.20 mL) was added dropwise over 15 min and after 1 h Ac-Glu(OSU)-OBzl (135 mg, 360 µmol). The reaction was allowed to warm to rt over 4 h and stirred over night at rt. After evaporation the residue was treated with aq. 10% KHSO₄ and EtOAc (3×). The organic phases were washed once with aq. 10% KHSO₄, sat. aq. NaHCO₃ and with aq. 10% NaCl, the combined organic phase was dried over Na₂SO₄, filtered and evaporated. The product was precipitated 2× from CH₂Cl₂ with Et₂O and n-pentane to give 253 mg (83%) white solid. ¹H NMR (300 MHz, DMSO-d6): δ=8.54 (t, J=6.6 Hz, 1H), 8.28 (d, J=7.5 Hz, 1H), 7.81 (t, J=6.2 Hz, 2H), 7.33-7.43 (m, 6H), 7.24-7.32 (m, 1H), 7.09-7.19 (m, 1H), 7.05 (d, J=6.3 Hz, 1H), 6.71 (s, 1H), 5.11 (s, 2H), 4.53-4.70 (m, 2H), 4.23 (d, J=12.3 Hz, 1H), 4.05 (br. s., 2H), 3.79-3.98 (m, 3H), 2.86-3.09 (m, 4H), 2.08-2.19 (m, 2H), 1.89-2.04 (m, 1H), 1.84 (s, 3H), 1.77 (s, 1H), 1.39 (s, 3H), 1.20 (d, J=5.9 Hz, 3H). LC-MS: 849.7 (M+H)⁺.

Step b) (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid (13a)

Under Argon and stirring (S)-benzyl 2-acetamido-5-(2-((2-((2R,3S)-7-fluoro-3-((S)-2-hydroxy-2-methyl-3-oxo-3-(2,2,3,3,3-pentafluoropropylamino) propanamido)-2-methyl-4-oxo-3,4-dihydrobenzo[b][1,4]oxazepin-5(2H)-yl)ethoxy)carbonylamino)ethylamino)-5-oxopentanoate (12a) (202 mg, 238 µmol) was dissolved in dioxane (3.81 mL) and MeOH (3.81 ml), Pd—C 10%, Typ E10N (20.2 mg, 190 µmol) was added and after evacuation and replacing with H₂ (5 times) the mixture was hydrogenated for 3.5 h then filtered, washed with MeOH and evaporated to afford after precipitation from CH₂Cl₂ with Et₂O the title compound compound (148 mg, 82%) as off-white solid. HPLC: tR 1.04 min, 99.2% (265 nm); tR 1.04 min, 98.2% (225 nm). 1H NMR (300 MHz, DMSO-d6): δ=8.72 (br. s., 1H), 7.86 (d, J=6.9 Hz, 1H), 7.81 (t, J=5.5 Hz, 1H), 7.44-7.52 (m, 1H), 7.42 (dd, J=9.7, 3.0 Hz, 1H), 7.28 (dd, J=8.9, 5.5 Hz, 1H), 7.14 (td, J=8.5, 2.9 Hz, 1H), 7.06 (t, J=5.6 Hz, 1H), 6.80 (br. s., 1H), 4.66 (t, J=6.8 Hz, 1H), 4.58 (quin, J=6.3 Hz, 1H), 4.17-4.25 (m, 1H), 4.02-4.10 (m, 1H), 3.93-4.00 (m, 1H), 3.82-3.93 (m, 4H), 3.01-3.08 (m, 2H), 2.91-3.00 (m, 2H), 2.03-2.09 (m, 2H), 1.85-1.91 (m, 1H), 1.82 (s, 3H), 1.66-1.76 (m, 1H), 1.38 (s, 3H), 1.22 (d, J=6.3 Hz, 3H). LC-MS: 759.6 (M+H)⁺. HRMS (C₂₉H₃₆F₆N₆O₁₁): calcd. 758.2346 [M]; found 758.2341.

Example 5

H-γ-Glu-Prodrug (H-γ-Glu-SecrI) 13b (S)-2-Amino-5-(2-((2-((2R,3S)-7-fluoro-34(S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid

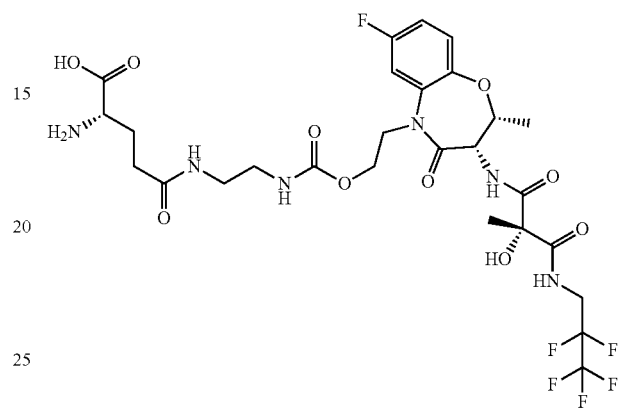

Step a) (S)-tert-Butyl-2-(tert-butoxycarbonylamino)-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (12b)

A solution of 2-((2R,3S)-7-fluoro-3-((S)-2-hydroxy-2-methyl-3-oxo-3-(2,2,3,3,3-pentafluoropropylamino) propanamido)-2-methyl-4-oxo-3,4-dihydrobenzo[b][1,4]oxazepin-5(2H)-yl)ethyl 2-aminoethylcarbamate hydrochloride (11a) (299 mg, 480 µmol) in DMF (5 mL) was treated with BOC-Glu-OtBu (160 mg, 528 µmol), 1-hydroxy-7-azabenzotriazole (65 mg, 480 µmol) and at 0° C. with EDCI (101 mg, 528 µmol). Et3N (74 µL, 528 µmol) in DMF (3.5 mL) was added very slowly in 3 portions offer 2 h. The reaction was allowed to warm to rt over night and extracted with aq. 10% KHSO4/Et2O (3×). The organic phase was washed with aq. sat. NaHCO3, 10% NaCl, dried over Na2SO4 and evaporated. The residue was precipitated from CH2Cl2 with Et2O an n-pentane to yield the title compound (422 mg, quantitative) as white solid. 1H NMR (300 MHz, DMSO-d6): δ=8.54 (t, J=6.4 Hz, 1H), 7.73-7.88 (m, 2H), 7.40 (dd, J=10.1, 3.0 Hz, 1H), 7.28 (dd, J=8.9, 5.7 Hz, 1H), 7.14 (td, J=8.3, 2.8 Hz, 1H), 6.99-7.10 (m, 2H), 6.71 (s, 1H), 4.53-4.72 (m, 2H), 4.14 (d, J=8.1 Hz, 1H), 4.02-4.09 (m, 2H), 3.81-3.99 (m, 3H), 3.70 (s, 1H), 2.88-3.09 (m, 4H), 2.11 (t, J=7.2 Hz, 2H), 1.79-1.96 (m, 1H), 1.59-1.77 (m, 1H), 1.36-1.44 (m, 21H), 1.20 (d, J=6.1 Hz, 4H). LC-MS: 871.6 (M−H−).

Step b) (S)-2-Amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid hydrochloride (13b)

To a solution of (S)-tert-butyl-2-(tert-butoxycarbonylamino)-5-(2-((2-((2R,3S)-7-fluoro-3-((S)-2-hydroxy-2- methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (12b) (320 mg, 367 µmol) in CH$_2$Cl$_2$ (6.8 mL) and dioxane (6.8 mL) at 0° C. was added drop wise a solution of 4M HCl in dioxane (1.8 mL, 7.3 mmol) and 1 drop of water. After 10 min, the reaction mixture was stirred for 21 h at 25° C. Again 4M HCl in dioxane (0.9 mL, 3.7 mmol) and 1 drop of water was added at 0° C. and after 3.5 h at rt, volatilities were evaporated off in vacuo. Resulting crude material was triturated 2× with CH$_2$Cl$_2$/Et$_2$O to yield the title compound (226 mg, 82%; 83% purity with 17% of the corresponding tert-butyl ester) as white solid. HPLC: tR 1.86 min, 82.9% (265 nm); tR 1.86 min, 83.4% (220 nm). $^1$H NMR (300 MHz, DMSO-d6): δ=13.80 (br s, 1H), 8.56 (t, J=6.55 Hz, 1H), 8.31 (br s, 3H), 8.00 (br t, J=5.49 Hz, 1H), 7.82 (d, J=6.85 Hz, 1H), 7.40 (dd, J=2.82, 9.67 Hz, 1H), 7.29 (dd, J=5.59, 8.92 Hz, 1H), 7.15 (dt, J=2.92, 8.41 Hz, 1H), 7.09 (br t, J=5.69 Hz, 1H), 6.74 (s, 1H), 4.66 (t, J=6.70 Hz, 1H), 4.56-4.63 (m, 1H), 4.11-4.22 (m, 1H), 4.06 (br t, J=5.69 Hz, 2H), 3.80-3.97 (m, 4H), 3.02-3.11 (m, 2H), 2.92-3.00 (m, 2H), 2.26-2.35 (m, 1H), 2.16-2.24 (m, 1H), 1.90-2.06 (m, 2H), 1.39 (s, 3H), 1.20 (d, J=6.25 Hz, 3H). $^{13}$C NMR (151 MHz, DMSO-d6) δ 171.9, 171.0, 170.8, 170.0, 167.6, 159.7, 158.1, 155.8, 146.1, 146.0, 136.4, 136.4, 123.8, 123.7, 114.2, 114.0, 111.0, 110.8, 83.1, 82.2, 76.5, 60.6, 51.6, 51.3, 46.6, 40.2, 40.0, 39.0, 38.6, 38.0, 30.6, 27.5, 25.9, 25.8, 23.5, 15.4. LC-MS: 717.3 (M+H)$^+$. HRMS (C$_{27}$H$_{34}$F$_6$N$_6$O$_{10}$): calcd. 716.2241 [M]; found 716.2255.

Example 6

Ac-α-Glu-Prodrug (Ac-α-Glu-SecrI) 15a (S)-4-acetamido-5-(2-((2-((2R,3S)-7-fluoro-34(S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid

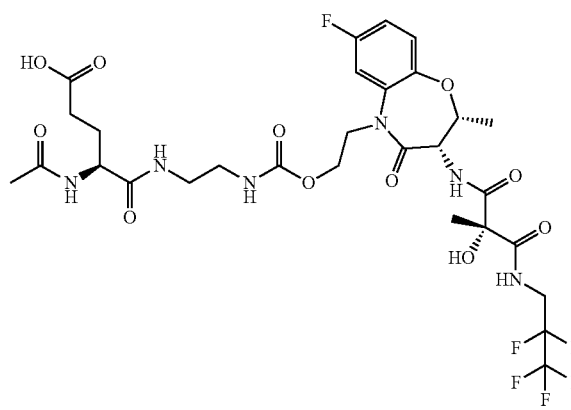

Step a) (S)-tert-Butyl 4-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (14a)

A solution of 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 2-aminoethylcarbamate hydrochloride (11a) (530 mg, 850 µmol) in DMF (16.1 mL) was treated with Ac-Glu(OtBu)-OH (229 mg, 935 µmol), 1-hydroxy-7-azabenzotriazole (116 mg, 850 µmol), Et$_3$N (130 µL, 935 µmol) and at 0° C. with EDCI (179 mg, 935 µmol). The reaction was allowed to warm to rt over night and extracted with aq. 10% KHSO$_4$/EtOAc (3×). The organic phases were washed with aq. sat. NaHCO$_3$, aq. 10% NaCl, dried over Na$_2$SO$_4$ and evaporated. The residue was precipitated from CH$_2$Cl$_2$ with Et$_2$O to yield the title compound (700 mg, quantitative). $^1$H NMR (300 MHz, DMSO-d6): δ=8.54 (t, J=6.5 Hz, 1H), 7.94 (d, J=8.1 Hz, 1H), 7.87 (t, J=5.7 Hz, 1H), 7.82 (d, J=6.5 Hz, 1H), 7.40 (dd, J=9.6, 2.9 Hz, 1H), 7.28 (dd, J=8.9, 5.7 Hz, 1H), 7.14 (ddd, J=8.6, 3.0 Hz, 1H), 7.03 (t, J=5.3 Hz, 1H), 6.71 (s, 1H), 4.53-4.75 (m, 2H), 4.10-4.23 (m, 2H), 4.06 (t, J=5.1 Hz, 2H), 3.76-3.98 (m, 3H), 2.85-3.16 (m, 4H), 2.10-2.22 (m, 2H), 1.83 (s, 3H), 1.79-1.93 (m, 1H), 1.57-1.75 (m, 1H), 1.39 (s, 3H), 1.38 (s, 9H), 1.20 (d, J=5.9 Hz, 3H). LC-MS: 815.3 (M+H$^+$).

Step b) (S)-4-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid (15a)

To a solution of (S)-tert-butyl 4-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino) ethylamino)-5-oxopentanoate (14a) (600 mg, 736 µmol) in CH$_2$Cl$_2$ (13.7 mL) and dioxane (13.7 mL) at 0° C. was added drop wise a solution of 4M HCl in dioxane (3.68 mL, 14.7 mmol) and 1 drop of water. After 10 min, the reaction mixture was stirred for 22 h at 25° C. Volatilities were evaporated off in vacuo. Resulting crude material was triturated with CH$_2$Cl$_2$/Et$_2$O to yield the title compound (455 mg, 81%) as white solid. HPLC: tR 2.09 min, 90.7% (265 nm); tR 2.09 min, 86.5% (220 nm). $^1$H NMR (600 MHz, DMSO-d6): δ=11.42-12.63 (m, 1H), 8.56 (t, J=6.50 Hz, 1H), 7.97 (d, J=8.06 Hz, 1H), 7.90 (br t, J=5.54 Hz, 1H), 7.82 (d, J=6.85 Hz, 1H), 7.40 (dd, J=2.87, 9.72 Hz, 1H), 7.29 (dd, J=5.59, 8.81 Hz, 1H), 7.14 (dt, J=3.02, 8.41 Hz, 1H), 7.05 (t, J=5.69 Hz, 1H), 6.73 (br s, 1H), 4.65 (t, J=6.75 Hz, 1H), 4.57-4.63 (m, 1H), 4.26-4.46 (m, 1H), 4.15 (dt, J=4.43, 8.81 Hz, 2H), 4.05 (br t, J=5.69 Hz, 2H), 3.84-3.96 (m, 3H), 2.89-3.12 (m, 4H), 2.63-2.76 (m, 1H), 2.13-2.24 (m, 2H), 1.81-1.94 (m, 4H), 1.63-1.72 (m, 1H), 1.39-1.41 (m, 1H), 1.39 (s, 2H), 1.20 (d, J=6.25 Hz, 3H). $^{13}$C NMR (151 MHz, DMSO-d6) δ 173.9, 171.8, 171.4, 170.0, 169.3, 167.6, 159.7, 158.1, 155.8, 146.0, 136.4, 136.4, 123.8, 123.7, 119.5, 117.6, 114.2, 114.0, 113.1, 112.9, 111.0, 110.8, 82.0, 76.5, 64.9, 60.6, 51.9, 51.3, 46.6, 38.5, 38.0, 30.2, 27.7, 27.3, 26.0, 23.5, 22.5, 15.4, 15.2. LC-MS: 759.3 (M+H)$^+$. HRMS (C$_{29}$H$_{36}$F$_6$N$_6$O$_{11}$): calcd. 758.23463 [M]; found 758.23636.

Example 7

H-α-Glu-Prodrug (H-α-Glu-SecrI) 15b (S)-4-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid

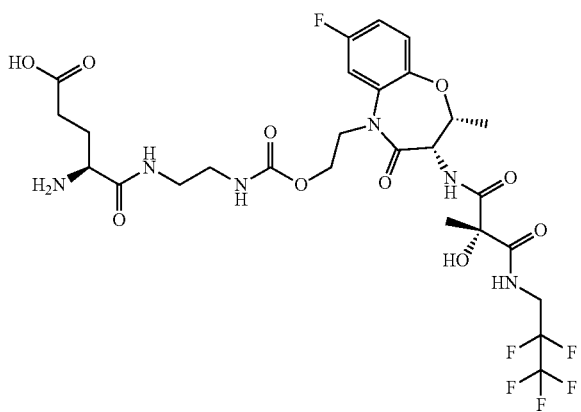 [SMILES: C[C@H]1Oc2ccc(F)cc2N(CCOC(=O)NCCNC(=O)[C@@H](N)CCC(=O)O)C(=O)[C@H]1NC(=O)[C@@](C)(O)C(=O)NCC(F)(F)C(F)(F)F]

Step a) (S)-tert-Butyl-4-(tert-butoxycarbonylamino)-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (14b)

A solution of 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 2-aminoethylcarbamate hydrochloride (11a) (265 mg, 425 μmol) in DMF (8 mL) was treated with BOC-Glu(OtBu)-OH (142 mg, 468 μmol), 1-hydroxy-7-azabenzotriazole (58 mg, 425 μmol), Et$_3$N (65 μL, 468 μmol) and at 0° C. with EDCI (90 mg, 468 μmol). The reaction was allowed to warm to rt over night and extracted with aq. 10% KHSO4/Et2O (3×). The organic phases were washed with aq. sat. NaHCO$_3$, aq. 10% NaCl, dried over Na$_2$SO$_4$ and evaporated. The residue was precipitated from CH$_2$Cl$_2$ with Et$_2$O an n-pentane to yield the title compound (373 mg, quantitative) as white solid. $^1$H NMR (300 MHz, DMSO-d6): δ=8.55 (t, J=6.6 Hz, 1H), 7.82 (d, J=6.7 Hz, 2H), 7.41 (dd, J=10.7, 2.4 Hz, 1H), 7.28 (dd, J=8.9, 5.7 Hz, 1H), 7.14 (td, J=8.3, 2.8 Hz, 1H), 7.01 (br. s., 1H), 6.80 (d, J=7.5 Hz, 1H), 6.71 (s, 1H), 4.55-4.72 (m, 2H), 4.11-4.23 (m, 1H), 4.07 (d, J=4.8 Hz, 2H), 3.77-3.99 (m, 4H), 2.91-3.16 (m, 3H), 2.18 (t, J=7.4 Hz, 2H), 1.74-1.89 (m, 1H), 1.54-1.72 (m, 1H), 1.35-1.41 (m, 21H), 1.20 (d, J=5.9 Hz, 3H). LC-MS: 871.6 (M–H$^-$).

Step b) (S)-4-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid hydrochloride (15b)

To a solution of (S)-tert-butyl-4-(tert-butoxycarbonylamino)-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoate (14b) (320 mg, 367 μmol) in CH$_2$Cl$_2$ (6.8 mL) and dioxane (6.8 mL) at 0° C. was added drop wise a solution of 4M HCl in dioxane (1.8 mL, 7.4 mmol) and 1 drop of water. After 10 min, the reaction mixture was stirred for 18 h at 25° C. Volatilities were evaporated off in vacuo. Resulting crude material was triturated with CH$_2$Cl$_2$/EtOAc to yield the title compound (222 mg, 80%; 88% purity with 12% corresponding tert-butyl ester) as white solid. HPLC: tR 1.76 min, 88.0% (265 nm); tR 1.76 min, 88.8% (220 nm). $^1$H NMR (300 MHz, DMSO-d6): δ=12.31 (br s, 1H), 8.56 (t, J=6.55 Hz, 1H), 8.53 (br t, J=5.59 Hz, 1H), 8.19 (br s, 3H), 7.82 (d, J=6.95 Hz, 1H), 7.40 (dd, J=2.77, 9.72 Hz, 1H), 7.29 (dd, J=5.59, 8.81 Hz, 1H), 7.08-7.19 (m, 2H), 6.74 (s, 1H), 4.66 (t, J=6.75 Hz, 1H), 4.58-4.64 (m, 1H), 4.11-4.20 (m, 1H), 4.00-4.10 (m, 2H), 3.83-3.98 (m, 3H), 3.72 (br d, J=5.44 Hz, 1H), 3.18 (td, J=6.45, 12.89 Hz, 1H), 3.07 (td, J=6.28, 12.92 Hz, 1H), 3.02 (q, J=6.45 Hz, 2H), 2.23-2.34 (m, 2H), 1.93 (q, J=7.35 Hz, 2H), 1.39 (s, 3H), 1.21 (d, J=6.15 Hz, 3H). $^{13}$C NMR (151 MHz, DMSO-d6) δ 173.2, 171.9, 170.0, 168.2, 167.6, 159.7, 158.1, 155.8, 146.0, 136.4, 123.8, 123.7, 114.2, 114.0, 110.9, 110.8, 82.2, 76.5, 60.7, 51.7, 51.3, 46.6, 40.0, 38.9, 38.9, 38.6, 38.2, 38.0, 29.1, 27.7, 26.1, 23.5, 15.4. LC-MS: 717.3 (M+H)$^+$. HRMS (C$_{27}$H$_{34}$F$_6$N$_6$O$_{10}$): calcd. 716.2241 [M]; found 716.2254.

Example 8 amine-γ-O-Secretase Inhibitor (amine-O-SecrI) 11b

2-Aminoethyl 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl carbonate hydrochloride

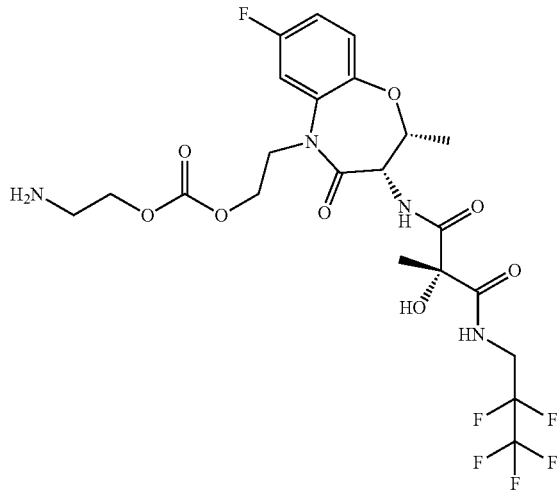 [SMILES: C[C@H]1Oc2ccc(F)cc2N(CCOC(=O)OCCN)C(=O)[C@H]1NC(=O)[C@@](C)(O)C(=O)NCC(F)(F)C(F)(F)F]

Step a) tert-Butyl 2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy) (10b)

To a solution of 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl 4-nitrophenyl carbonate (9) (Example 3; step a) (666 mg, 1.00 mmol) in CH$_2$Cl$_2$ (8.3 mL) at 0° C. under argon atmosphere were added DMAP (110 mg, 0.90 mmol) and drop wise a solution of N-BOC-glycinol (178 μL, 1.10 mmol) in CH$_2$Cl$_2$ (5 mL) and Et$_3$N (193 μL, 1.00 mmol). Resultant reaction mixture was stirred at 0° C. for 1 h followed by another 12 h at 25° C. Again DMAP (12.2 mg, 0.10 mmol) and a solution of N-BOC-glycinol (32 μL, 0.20 mmol) in CH$_2$Cl$_2$ (0.7 mL) were added at 0° C., stirred for 5 h at 25° and then poured into aq. 10% KHSO$_4$ (10 mL). Organic layer was separated, and the aq. layer was re-extracted with EtOAc (2×20 mL). Combined organic layer was dried over anhydrous Na$_2$SO$_4$, filtered, and evaporated off in vacuo. Resulting crude material was purified by flash chromatography (130 g SiO$_2$, Cilicycle-cartridge, CH$_2$Cl$_2$/Et$_2$O 6:1) to afford the title compound (530 g, 77%) as white foam. HPLC: tR 1.43 min, 100% (225 nm). HRMS (C$_{27}$H$_{34}$F$_6$N$_4$O$_{10}$): calcd. 688.2179[M]; found 688.218.

Step c) 2-Aminoethyl 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl carbonate hydrochloride (11b)

To a solution of tert-butyl 2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy) (10b) (511 mg, 0.74 mmol) in CH$_2$Cl$_2$ (2.8 mL) at 0° C. was added drop wise a solution of 4M HCl in dioxane (1.86 mL). Reaction mixture was stirred for 3.5 h at 0° C. and 0.5 h at 25° C. Volatilities were evaporated off in vacuo. Resulting crude material was triturated with CH$_2$Cl$_2$/Et$_2$O to yield the title compound (424 mg, 91%) as white powder. HPLC: tR 0.85 min, 100% (225 nm). HRMS (C$_{22}$H$_{26}$F$_6$N$_4$O$_8$): calcd. 588.1655[M]; found 588.1652.

Example 9

Ac-γ-Glu-O-Prodrug (Ac-γ-Glu-O-SecrI) 13c (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoic acid

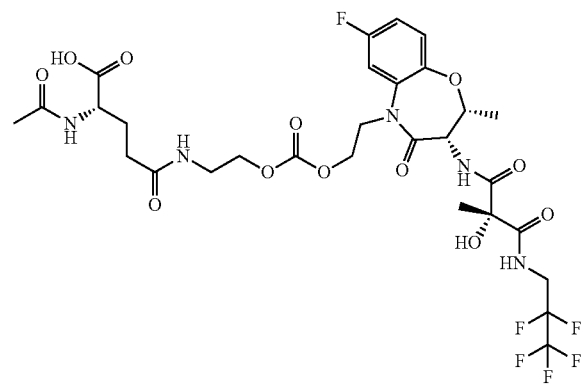 [SMILES: CC(=O)N[C@@H](CCC(=O)NCCOC(=O)OCCN1C(=O)[C@@H](NC(=O)[C@@](C)(O)C(=O)NCC(F)(F)C(F)(F)F)[C@@H](C)Oc2ccc(F)cc21)C(=O)O]

Step a) (S)-Methyl 2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoate (12c)

A solution of 2-aminoethyl 2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethyl carbonate hydrochloride (11b) (313 mg, 501 μmol) in DMF (9.5 mL) was treated with Ac-Glu-OMe (112 mg, 551 μmol), 1-hydroxy-7-azabenzotriazole (68 mg, 501 μmol) and at 0° C. with EDCI (115 mg, 601 μmol). Et$_3$N (70 μL, 501 μmol) was added very slowly. The reaction was allowed to warm to rt over night and extracted with aq. 10% KHSO$_4$/EtOAc (3×). The organic phase was washed with aq. sat. NaHCO3, 10% NaCl, dried over Na2SO4 and evaporated. Resulting crude material was purified by flash chromatography (130 g SiO$_2$, Cilicycle-cartridge, CH$_2$Cl$_2$/MeOH 2 to 5%) to afford the title compound (300 mg, 52%) as white foam. HPLC: tR 1.13 min, 100% (225 nm). HRMS (C$_{30}$H$_{37}$F$_6$N$_5$O$_{12}$): calcd. 773.2343 [M]; found 773.2333.

Step b) (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoic acid (13c)

To a solution of (S)-methyl 2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoate (12c). (62 mg, 80.1 μmol) in THF (0.2 mL) at 0° C. was added drop wise aq. 1N LiOH (72.1 μL, 72.1 μl). The reaction was extracted after 3.75 h (0° C.) with aq. 10% KHSO$_4$/EtOAc (3×). The organic phase was washed with aq. 10% NaCl, dried over Na2SO4 and evaporated. Resulting crude material was purified by flash chromatography (10 g SiO$_2$, Cilicycle-cartridge, CH$_2$Cl$_2$/MeOH 5 to 25%) to afford the title compound (17 mg, 28%) as white foam. HPLC: tR 1.06 min, 100% (225 nm). HRMS (C$_{29}$H$_{35}$F$_6$N$_5$O$_{12}$): calcd. 759.2186 [M]; found 759.2181.

Example 10

γ-Secretase Inhibitors of Formula (A)

Alternative γ-secretase inhibitor alcohols of formula (A) have been prepared as described in WO 2006/061136 A2 according to Table 1 below.

TABLE 1

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 53 | p. 70-72 | 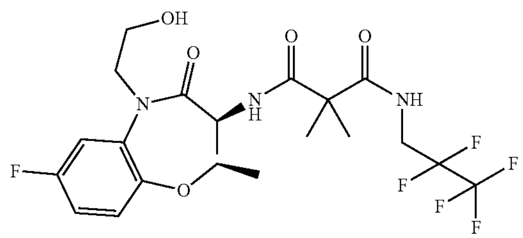 | N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide |
| 66a | p. 88-90 | 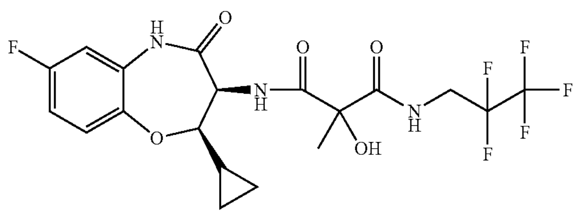 [SMILES: CC(O)(C(=O)NCC(F)(F)C(F)(F)F)C(=O)N[C@@H]1C(=O)Nc2cc(F)ccc2O[C@@H]1C1CC1] | N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide |
| 66b | p. 88-90 | 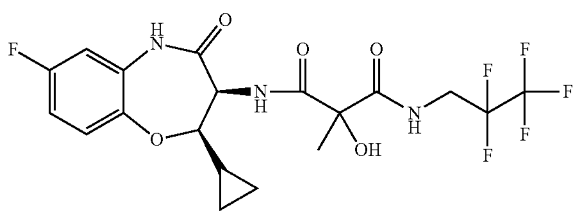 [SMILES: CC(O)(C(=O)NCC(F)(F)C(F)(F)F)C(=O)N[C@@H]1C(=O)Nc2cc(F)ccc2O[C@@H]1C1CC1] | N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide |
| 70a (SecrI 8) | p. 95-97 | 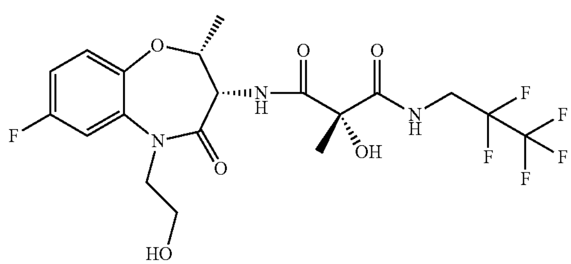 [SMILES: C[C@H]1Oc2ccc(F)cc2N(CCO)C(=O)[C@H]1NC(=O)[C@@](C)(O)C(=O)NCC(F)(F)C(F)(F)F] | (S)-N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide |
| 70b | p. 95-97 | 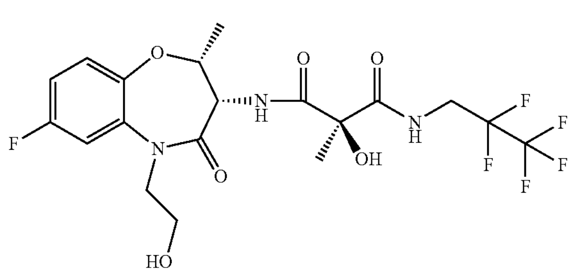 [SMILES: C[C@H]1Oc2ccc(F)cc2N(CCO)C(=O)[C@H]1NC(=O)[C@](C)(O)C(=O)NCC(F)(F)C(F)(F)F] | (R)-N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide |

TABLE 1-continued

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 71a | p. 97-98 | 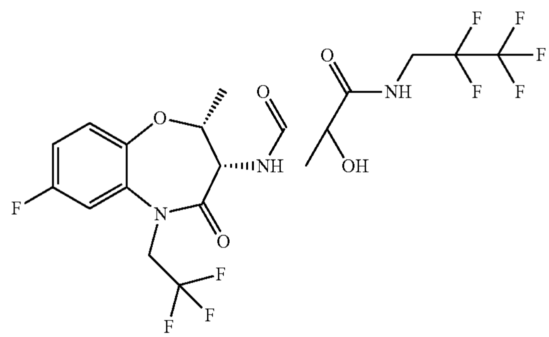 | (R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide |
| 71b | p. 97-98 | 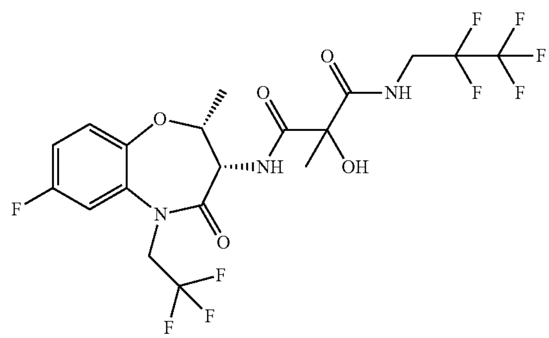 [SMILES: C[C@H]1Oc2ccc(F)cc2N(CC(F)(F)F)C(=O)[C@H]1NC(=O)C(C)(O)C(=O)NCC(F)(F)C(F)(F)F] | (R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide |
| 72a | p. 99-100 | 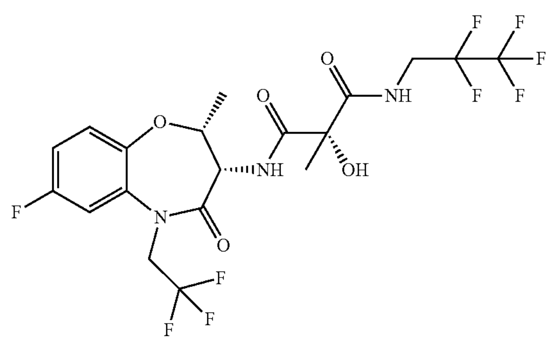 [SMILES: C[C@H]1Oc2ccc(F)cc2N(CC(F)(F)F)C(=O)[C@H]1NC(=O)[C@@](C)(O)C(=O)NCC(F)(F)C(F)(F)F] | (S)-N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide |
| 72b | p. 99-100 | 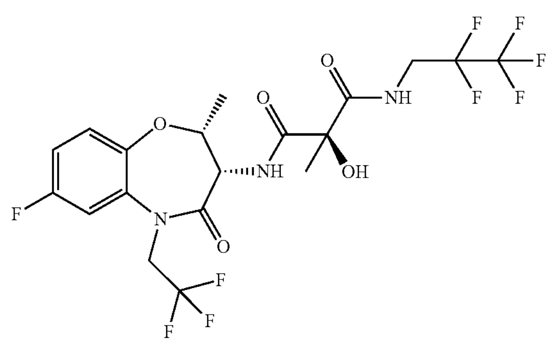 [SMILES: C[C@H]1Oc2ccc(F)cc2N(CC(F)(F)F)C(=O)[C@H]1NC(=O)[C@](C)(O)C(=O)NCC(F)(F)C(F)(F)F] | (R)-N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide |

TABLE 1-continued

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 73a | p. 101-102 | 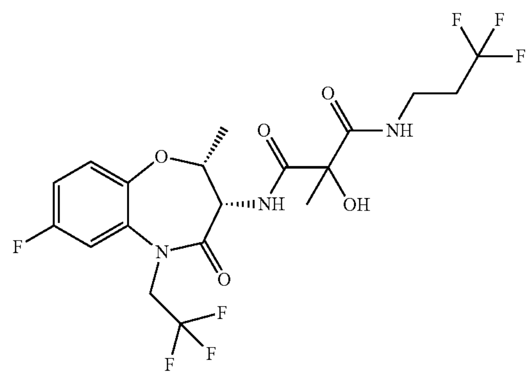 [SMILES: C[C@H]1Oc2ccc(F)cc2N(CC(F)(F)F)C(=O)[C@H]1NC(=O)C(C)(O)C(=O)NCCC(F)(F)F] | (R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide |
| 73b | p. 101-102 | 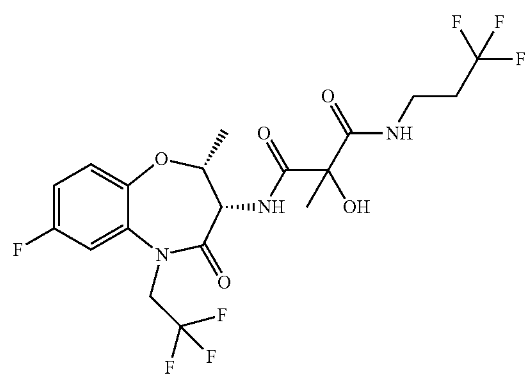 [SMILES: C[C@H]1Oc2ccc(F)cc2N(CC(F)(F)F)C(=O)[C@H]1NC(=O)C(C)(O)C(=O)NCCC(F)(F)F] | (R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide |
| 74 | p. 102-104 | 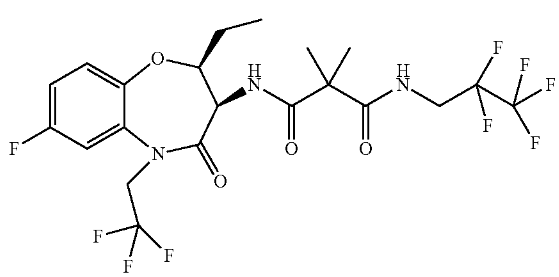 [SMILES: CC[C@@H]1Oc2ccc(F)cc2N(CC(F)(F)F)C(=O)[C@@H]1NC(=O)C(C)(C)C(=O)NCC(F)(F)C(F)(F)F] | N-[(6S,7R)-6-Ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide |
| 75a | p. 105-106 | 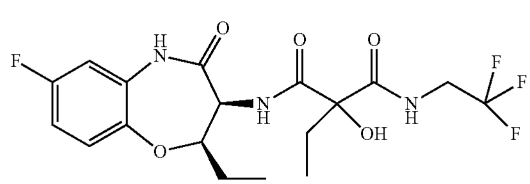 [SMILES: CC[C@H]1Oc2ccc(F)cc2NC(=O)[C@H]1NC(=O)C(O)(CC)C(=O)NCC(F)(F)F] | (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide |
| 75b | p. 105-106 | 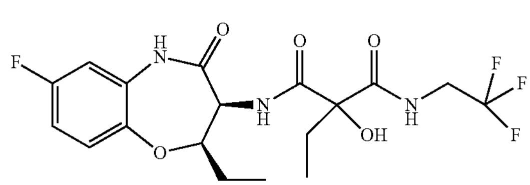 [SMILES: CC[C@H]1Oc2ccc(F)cc2NC(=O)[C@H]1NC(=O)C(O)(CC)C(=O)NCC(F)(F)F] | (S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide |

TABLE 1-continued

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 76a | p. 106-107 | 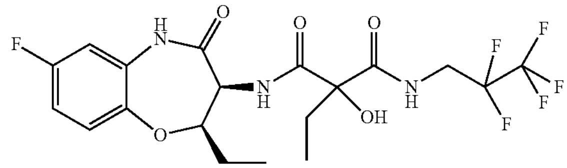 [SMILES: CC[C@H]1Oc2ccc(F)cc2NC(=O)[C@H]1NC(=O)C(O)(CC)C(=O)NCC(F)(F)C(F)(F)F] | (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide |
| 76b | p. 106-107 | 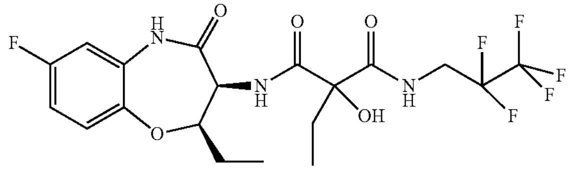 [SMILES: CC[C@H]1Oc2ccc(F)cc2NC(=O)[C@H]1NC(=O)C(O)(CC)C(=O)NCC(F)(F)C(F)(F)F] | (S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide |
| 77a | p. 107-108 | 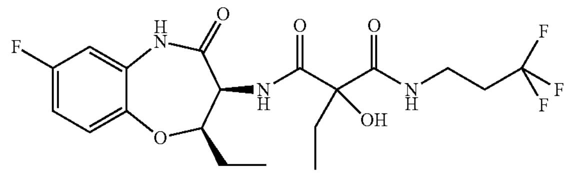 [SMILES: CC[C@H]1Oc2ccc(F)cc2NC(=O)[C@H]1NC(=O)C(O)(CC)C(=O)NCCC(F)(F)F] | (R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide |
| 77b | p. 107-108 | 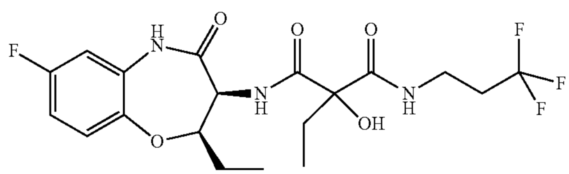 [SMILES: CC[C@H]1Oc2ccc(F)cc2NC(=O)[C@H]1NC(=O)C(O)(CC)C(=O)NCCC(F)(F)F] | (S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide |
| 78a | p. 108-109 | 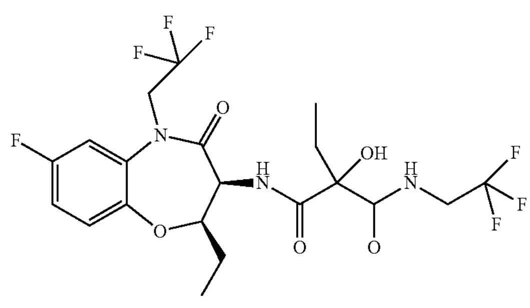 [SMILES: CC[C@H]1Oc2ccc(F)cc2N(CC(F)(F)F)C(=O)[C@H]1NC(=O)C(O)(CC)C(O)NCC(F)(F)F] | (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide |
| 78b | p. 108-109 | 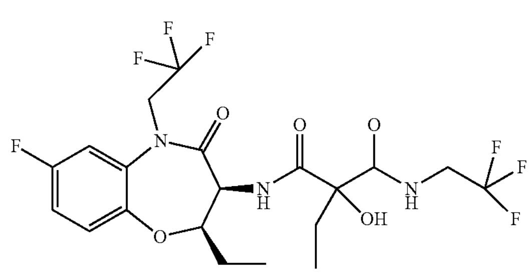 [SMILES: CC[C@H]1Oc2ccc(F)cc2N(CC(F)(F)F)C(=O)[C@H]1NC(=O)C(O)(CC)C(O)NCC(F)(F)F] | (S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide |

TABLE 1-continued

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 79a | p. 109-110 | 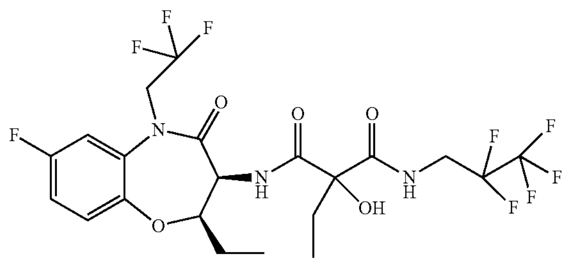 [SMILES: CC[C@H]1Oc2ccc(F)cc2N(CC(F)(F)F)C(=O)[C@H]1NC(=O)C(O)(CC)C(=O)NCC(F)(F)C(F)(F)F] | (R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide |
| 79b | p. 109-110 | 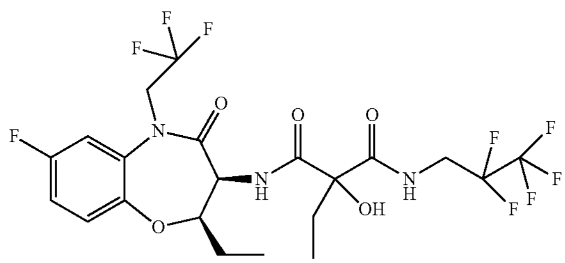 [SMILES: CC[C@H]1Oc2ccc(F)cc2N(CC(F)(F)F)C(=O)[C@H]1NC(=O)C(O)(CC)C(=O)NCC(F)(F)C(F)(F)F] | (S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide |
| 80 | p. 110-112 | 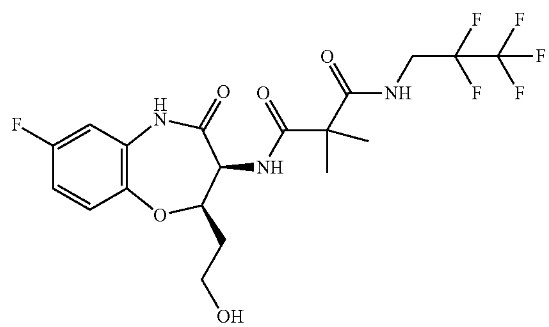 [SMILES: CC(C)(C(=O)NCC(F)(F)C(F)(F)F)C(=O)N[C@@H]1C(=O)Nc2cc(F)ccc2O[C@@H]1CCO] | N-[(6R,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide |
| 81 | p. 112-113 | 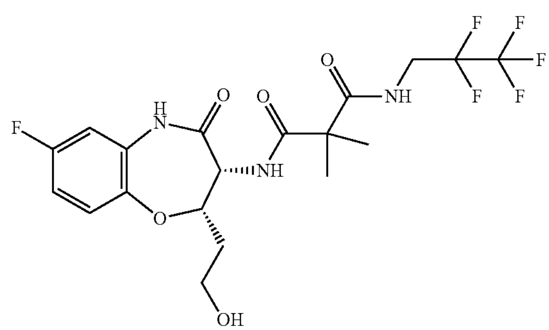 [SMILES: CC(C)(C(=O)NCC(F)(F)C(F)(F)F)C(=O)N[C@H]1C(=O)Nc2cc(F)ccc2O[C@H]1CCO] | N-[(6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide |
| 82a | p. 113 | 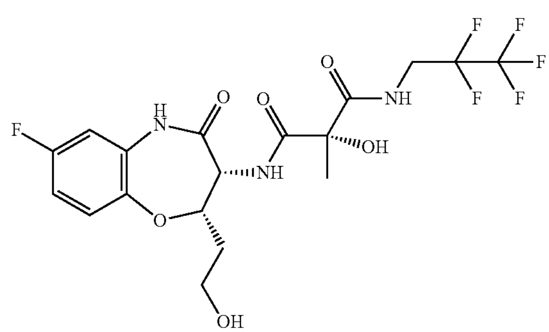 [SMILES: C[C@](O)(C(=O)NCC(F)(F)C(F)(F)F)C(=O)N[C@H]1C(=O)Nc2cc(F)ccc2O[C@H]1CCO] | (S)-N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide |

TABLE 1-continued

Preparation of γ-secretase inhibitor alcohols of formula A as described in WO 2006/061136 A2.

| Example No. in WO2006/ 061136A2 | Preparation described in WO2006/ 061136A2 | Structure | Compound Name |
|---|---|---|---|
| 82b | p. 113 | 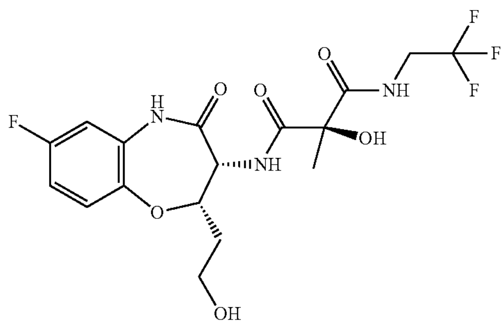 [SMILES: C[C@@](O)(C(=O)NCC(F)(F)F)C(=O)N[C@H]1C(=O)Nc2cc(F)ccc2O[C@H]1CCO] | (R)-N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide |
| 83a | p. 114 | 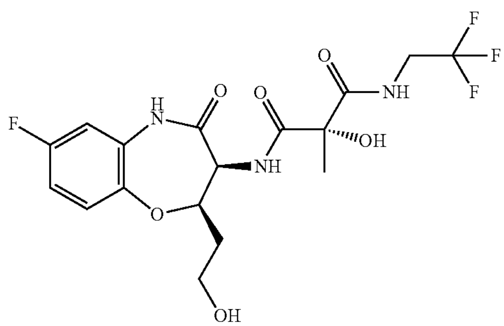 [SMILES: C[C@](O)(C(=O)NCC(F)(F)F)C(=O)N[C@@H]1C(=O)Nc2cc(F)ccc2O[C@@H]1CCO] | (S)-N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide |
| 83b | p. 114 | 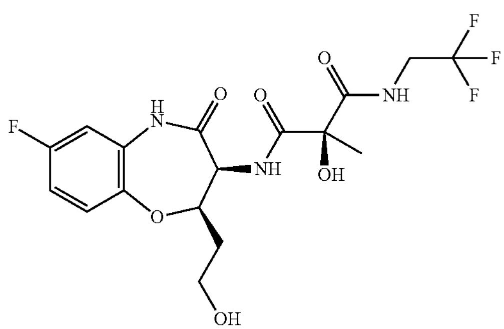 [SMILES: C[C@@](O)(C(=O)NCC(F)(F)F)C(=O)N[C@@H]1C(=O)Nc2cc(F)ccc2O[C@@H]1CCO] | (R)-N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide |
| 84a | p. 114-117 | 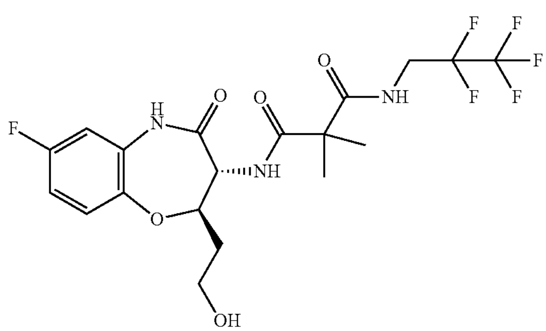 [SMILES: CC(C)(C(=O)NCC(F)(F)C(F)(F)F)C(=O)N[C@H]1C(=O)Nc2cc(F)ccc2O[C@@H]1CCO] | N-[(6R,7R) or (6S, 7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide |

TABLE 1-continued

Preparation of γ-secretase inhibitor alcohols of formula A as described in WO 2006/061136 A2.

| Example No. in WO2006/061136A2 | Preparation described in WO2006/061136A2 | Structure | Compound Name |
|---|---|---|---|
| 84b | p. 114-117 | 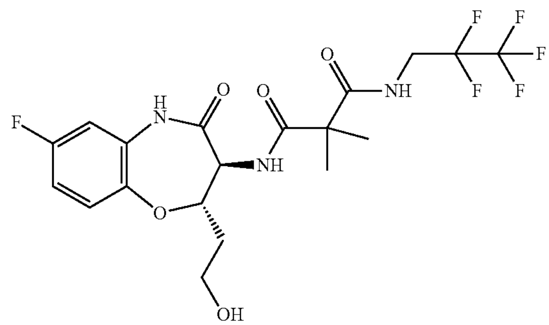 [SMILES: CC(C)(C(=O)NCC(F)(F)C(F)(F)F)C(=O)N[C@@H]1C(=O)Nc2cc(F)ccc2O[C@H]1CCO] | N-[(6S,7S) or (6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide |
| 85a | p. 117-118 | 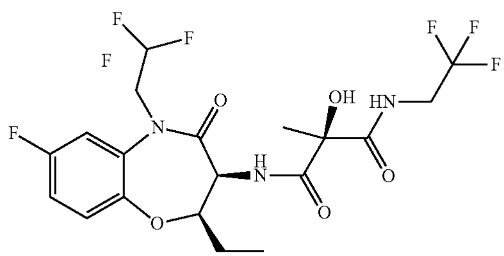 | (S)-N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide |
| 85b | p. 117-118 | 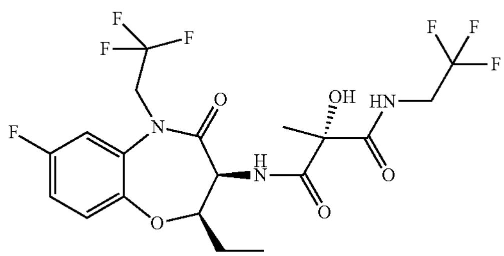 [SMILES: CC[C@H]1Oc2ccc(F)cc2N(CC(F)(F)F)C(=O)[C@H]1NC(=O)[C@](C)(O)C(=O)NCC(F)(F)F] | (R)-N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide |

Preparation of γ-secretase inhibitor alcohols of formula A as described in WO 2006/061136 A2.

Example 11

In Vitro γ-Secretase Activity Assay

The γ-secretase activity of the γ-secretase inhibiting alcohols of formula (A) of present invention was determined in cell-free in vitro assays where e.g., a cell lysate containing the γ-secretase complex is incubated with a suitable β-Amyloid Precursor Protein (APP)-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6×Histidin tail for purification which is expressed in E. coli in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998)).

IC50 activity values of γ-secretase inhibiting alcohols of formula (A) of present invention are disclosed in Table 2.

TABLE 2

IC50 values of the γ-secretase inhibiting alcohols of formula (A).

| Example No. in WO2006/061136A2 | IC50 [nM] in vitro | Example No. in WO2006/061136A2 | IC50 in vitro |
|---|---|---|---|
| 53 | 90 | 77a | 120 |
| 66a | 1201 | 77b | 20 |
| 66b | 30 | 78a | 19 |
| 70a (SecrI 8) | 7 | 78b | 130 |
| 70b | 625 | 79a | 14 |
| 71a | 28 | 79b | 90 |
| 71b | 580 | 80 | 230 |
| 72a | 390 | 81 | >20'000 |

TABLE 2-continued

IC50 values of the γ-secretase inhibiting alcohols of formula (A).

| Example No. in WO2006/061136A2 | IC50 [nM] in vitro | Example No. in WO2006/061136A2 | IC50 in vitro |
|---|---|---|---|
| 72b | 400 | 82a | >20'000 |
| 73a | 130 | 82b | |
| 73b | 1565 | 83a | 700 |
| 74 | 25 | 83b | 10210 |
| 75a | 420 | 84a | >20'000 |
| 75b | 60 | 84b | 30700 |
| 76a | 50 | 85a | 20 |
| 76b | 5 | 85b | 500 |

Example 12

In Vitro Notch Signal Transduction Pathway Activity Assay

Preparation of the γ-Secretase Inhibitor Analogues for In Vitro Experiments.

The compounds were dissolved in dimethyl sulfoxide (DMSO) at 10 mM stock solution, aliquoted and stored at −4° C. until use, then diluted in PBS or cell culture medium. In the experimental settings, controls containing increasing concentrations of DMSO, corresponding to the amount of DMSO of the diluted compounds were always included. For in vivo experiments, the compounds were dissolved in 0.9% NaCl, incubated 30 min at 40° C. and sonicated for 5 min.

In Vitro Notch Signal Transduction Pathway Activity Assay

The requirement of proteolytic activation of the prodrugs to inhibit Notch cleavage by the γ-secretase, was investigated using a reporter assay (Table 3). The DR215/F2 cell line expresses a reporter construct designed to monitor the activity of the Notch signal transduction pathway. The DR215/F2 cell line 39 carries two transgenes: the firefly luciferase reporter gene expressed under the control of the Gal4 promoter and the human Notch1 activator gene fused with the yeast Gal4 transcription factor. This assay confirmed that the prodrugs were able to inhibit γ-secretase and the activation of the Notch pathway. The DR215/F2 cell reporter assay was also used to determine the IC50 for blockade of the Notch pathway by all the compounds designed and prepared. The free γ-secretase inhibitor and the amine-γ-SecrI and amine-O-γ-SecrI demonstrated inhibition in the low nanomolar range, whereas the non-hydrolyzed prodrugs were much less active, displaying IC50 values in the high nM range for the Ac-α-Glu-SecrI (15a) and the H-α-Glu-SecrI (15b) and even in the µM range for the H-γ-Glu-SecrI (13b) and Ac-γ-Glu-SecrI (13a) (Table 3).

TABLE 3

IC50 values of the γ-secretase inhibitors and prodrugs.

| | Compound | IC$_{50}$ [nM] |
|---|---|---|
| 8 | SecrI | 4.4 |
| 11a | amine-SecrI | 45.6 |
| 11b | amine-O-SecrI | 0.5 |
| 13a | Ac-γ-Glu-SecrI | 2882 |
| 13b | H-γ-Glu-SecrI | 1087 |
| 13c | Ac-γ-Glu-O-SecrI | 170 |
| 15a | Ac-α-Glu-SecrI | 625 |
| 15b | H-α-Glu-SecrI | 258 |

The values were determined using the 215/F2 reporter cell line for Notch activation by the γ-secretase. All values are the mean of at least 3 experiments.

Example 13

Extracellular Release of the γ-Secretase Inhibitor from Prodrugs

Cells and In Vitro Assays

The preparation and characterization of rat brain-derived EC219 endothelial cells have been described in Juillerat-Jeanneret, L. et al. In Vitro Cell. Dev. Biol. 1992, 28A, 537-543. These cells express high levels of APA and γ-GT activities and can be used for determining kinetics in living cells, and were chosen as APA- and γ-GT-positive representative cell models. EC219 cells were grown in DMEM medium containing 1 g/l glucose, 10% heat-inactivated fetal calf serum (FCS, EuroClone, UK) supplemented with 100 U/mL penicillin and 100 µg/mL streptomycin (P/S) on uncoated cell culture plastic ware. The HEK293 and HK2 human kidney cells are available from the ATCC (American Tissue Culture Collection, Manassas, Va., USA). HEK293 cells were grown on uncoated cell culture plastic ware in Iscove modified Dulbecco medium (IMDM, Life Technologies) containing 10% FCS and P/S. HK2 cells were grown on uncoated cell culture plastic ware in DMEM/F-12 GlutaMAX medium (Gibco) containing 5% FCS, P/S, 1% ITS (1.0 mg/ml bovine insulin, 0.55 mg/ml human transferrin and 0.5 µg/ml sodium selenite, Sigma-Aldrich) and 5 ng/ml hydrocortisone. The human HEK293-derived DR215/F2 embryonic kidney cell line, stably transfected with pFR Luc and APP-Notch Gal (plasmid DR215) as described in WO 2006/061136 A2 and Brockhaus, M. Neuroreport 1998 9, 1481-1486, were maintained using IMDM with 10% FCS supplemented with P/S and kept under double-selection with 150 µg/ml G-418 and 50 µg/ml hygromycin B on coated (1:100 Poly-L-lysine) cell culture plastic ware. In this assay, the Notch-Gal4 protein is bound to the cell membrane via its trans-membrane domain. The Notch intracellular domain is released by proteolytic cleavage mediated by the γ-secretase and moves to the cell nucleus where it activates the reporter luciferase gene transcript. Inhibition of γ-secretase thus decreases luciferase activity. Briefly, cultures were grown in 96-well microplates to 80% confluence; the cells were then washed in PBS and exposed to decreasing concentrations of the γ-secretase-inhibitor analogues in complete IMDM culture medium without red phenol at 37° C. for 19 h. Then 75 µl of supernatant from each well was removed and the luciferase activity was determined by adding 25 µl of Steady-Glo luciferase assay reagent (Promega). After incubation at room temperature (180 min for the IC50 determination, 20 min for the evaluation of Notch activation), the luminescence of individual microwells was measured in a microplate luminometer (SpectraMax Paradigm, Molecular Devices) or Synergy Mx (Monochromator, Biotek), for IC50 and Notch activation, respectively, and the values were analyzed using the Graphpad software.

Histoenzymography

Evaluation by histoenzymography of APA and γ-GT enzymatic activities on frozen tissue was performed as described in Juillerat-Jeanneret, L. et al., Lab. Invest. 2000, 80, 973-980. Briefly, OCT-embedded frozen kidneys were cut in 7 µm sections in a cryostat, fixed for 5 min in cold (−20° C.) acetone, air dried at RT and rehydrated for 5 min in 0.9% NaCl. Naphthylamide substrates were obtained from commercial sources (α-Glu-4-methoxy-β-naphtylamide (APA)

from Bachem; and γ-Glu-4-methoxy-β-naphtylamide (γ-GT) from Serva). Substrates (1 mg) were dissolved in 1 ml DMF and 2 mg Fast Blue B (Sigma-Aldrich) was dissolved in 2 ml 0.2M cacodylate buffer pH 7.4 containing 700 mg/l CaCl2; then both solutions were slowly mixed immediately before use and the pH adjusted to 6.5-7.0. The solution was filtered if some precipitation occurred, added to the slides and incubated in a humidified atmosphere at 37° C. for 15 to 60 min until a red coloration was visible. The slides were washed in distilled water, counter-stained with hematoxylin (Mayer) for 1 min, rinsed under tap water, then with Scott solution for 1 min, rinsed under tap water, mounted in Aquamount (Immu-mount, Thermo Shandon Pittsburgh, Pa., USA) and analyzed with a Nikon Eclipse E800 microscope and digital DXM1200 camera using ACT-1 software.

Extracellular Release of the γ-Secretase Inhibitor from Prodrugs

A first screen of the different γ-secretase prodrugs was performed in vitro to determine the cleavage rate of each compound and ex-vivo in mouse kidney tissues. Extracellular release of the γ-secretase inhibitor from prodrugs by human kidney cells (HEK293, HEK293-derived Notch-reporter 215/F2 cells28,39 and HK2 cells) as well as the rat brain-derived EC219 endothelial cells which express very high levels of APA and γ-GT activities were evaluated for liberating active inhibitors SecrI (8) or amine-SecrI (11a) (FIG. 2A). The EC219 and HK2 cells, but not the HEK293 cells, were able to release the amine-SecrI (11a) from the H-α-Glu-SecrI (15b) into the extracellular space, but not the free inhibitor (8), in a pattern involving APA activity. The Ac-α-Glu (15a) derivative was not a substrate for this enzyme and the Ac-γ-Glu-SecrI (13a) derivative was not hydrolyzed by γ-GT. But more surprisingly, the free H-γ-Glu-SecrI (15a) was also not hydrolyzed by γ-GT.

To confirm that the Ac-γ-Glu-SecrI (13a) may be a substrate for relevant cellular enzymatic activities, we determined if the Ac-γ-Glu-SecrI (13a) prodrug may inhibit the hydrolysis of α-Glu-naphthylamide and γ-Glu-naphthylamide derivatives by enzymohistochemistry, APA activity as a negative enzymatic control and amine-SecrI (11a) as a drug for negative control in ex-vivo kidneys of non-diseased mice (FIG. 2B). Only the Ac-γ-Glu-SecrI (13a), but not the Ac-α-Glu-SecrI (15a) or the amine-SecrI (11a), was able to inhibit γ-GT-like activity, while APA activity was not inhibited by any compound. Thus, these results clearly showed that the Ac-γ-Glu-SecrI (13a) prodrug inhibited the extracelluar activity of γ-GT and/or the intracellular γ-GCT activity, suggesting that the release of the active inhibitor is performed inside cells.

Example 14

Pharmacokinetic Assessment in C57BL/6 Healthy Wild-Type Mice and Male Wistar Rats Quantification and Pharmacokinetics (PK) of the γ-Secretase Inhibitor and its Analogues in Cells and in Mouse or Male Wistar Rat Plasma, Liver and Kidney.

All samples were analyzed using protein precipitation followed by LC-MS/MS analysis. After incubation with the cells, the extracellular medium was collected and quenched with 3 volumes of acetonitrile containing oxazepam at 100 ng/ml as Internal Standard (ISTD). Prepared samples were stored at −20° C. before analysis. After thawing at room temperature (RT), samples were stirred and centrifuged at 5600 rpm (6° C., 10 min). One μL of the supernatant was analyzed by LC/MS. The LC column and conditions used were: Phenomenex, Polar RP, 4 μm, 50×1 mm at 0.15 mL/min flow rate with a 1 min nonlinear gradient from 100% solvent A to 100% solvent B (Solvent A: Water/Methanol/HCOOH, 95:5:0.5; Solvent B: Methanol). Mass spectrometric conditions were: ABSciex API4000 with positive heated electrospray ionization in MS/MS mode. Compound mass transitions monitored were as described in Table 4:

TABLE 4

| Compound mass transitions | | | |
|---|---|---|---|
| | Transition Q1/Q3 (m/z→m/z) | Collision Energy (eV) | RT (min) |
| Oxazepam (ISTD) | 287.0/241.2 | 33 | 0.79 |
| SecrI (8) | 502.2/484.2 | 23 | 0.78 |
| amine-SecrI (11a) | 588.2/484.1 | 35 | 0.77 |
| H-α-Glu-SecrI (15b) | 717.0/484.2 | 45 | 0.76 |
| Ac-α-Glu-SecrI (15a) | 759.2/484.2 | 50 | 0.77 |
| H-γ-Glu-SecrI (13b) | 717.1/484.2 | 45 | 0.75 |
| Ac-γ-Glu-SecrI (13a) | 759.2/484.1 | 33 | 0.77 |

Relative concentration of the incubated drug and metabolites was established by percentage of peak area ratio compared to time zero spiked compounds.

For PK evaluation, the compounds were administered i.p to male C57BL/6 mice in suspension (gelatine/saline 7.5%/0.62% in water) using an administration volume of 4 mL/kg. Blood samples were collected in tubes containing EDTA, plasma was separated by centrifugation and stored at −80° C. Liver and kidney samples (~100 mg aliquots) were homogenized in three volumes of water using Precellys tissue homogenization tubes (precellys.com). 25 μL of each tissue homogenate was further diluted with 25 μL blank plasma to produce the final tissue homogenate for extraction. All samples were analyzed using protein precipitation followed by LC-MS/MS analysis. Briefly, 50 μL plasma or final tissue homogenate were mixed with 50 μL 0.5M HClO$_4$/acetonitrile 9/1 (containing 200 ng/mL internal standard bosentan). Samples were stirred and 300 μL water was added followed by centrifugation at 5600 rpm (4° C., 10 min). 10 μL supernatant was analyzed by LC/MS analysis. Calibration standards in plasma were prepared the same way. The LC column and conditions used were: Phenomenex, Polar RP, 4 μm, 50×2.1 mm at 0.4 mL/min flow rate with a 3 min gradient from 95% solvent A to 95% solvent B (Solvent A: Water/ACN/HCOOH, 90:10:0.1+10 mM NH$_4$ formate; Solvent B: Water/ACN/HCOOH, 10:90:0.1+10 mM NH$_4$ formate). Mass spectrometric conditions were: Thermo TSQ Vantage with positive heated electrospray ionization in MS/MS mode. Compounds mass transitions monitored were m/z 320.7 to 119.9. PK parameters for all studies were calculated using Phoenix WinNonlin Software.

Pharmacokinetic Assessment in C57BL/6 Healthy Wild-Type Mice

We next determined the stability, tissue distribution and cleavage rate in plasma, liver and kidney of the designed prodrugs in non-diseased mice. In the in vivo screen, the kinetics and distribution of γ-secretase inhibitor prodrugs Ac-γ-Glu-SecrI (13a), Ac-α-Glu-SecrI (15a) and H-α-Glu-SecrI (15b) were compared with the active γ-secretase inhibitor amine-SecrI (11a). After i.p administration (10 mg/kg) in C57BL/6 mice, the disappearance of the prodrugs and the formation of the active amine-SecrI (11a) were compared in plasma, liver and kidney (Table 5). First, we determined the pharmacokinetics (PK) behavior of amine-SecrI (11a) following i.p. administration (Table 5A). As expected, amine-SecrI (11a) had very low plasma exposure, indicating rapid plasma clearance. Liver and kidney exposure were much higher, with approximately 4.5-fold higher exposure in liver compared to kidney. As expected for the prodrug Ac-γ-Glu-SecrI (13a), we saw at 0.5 h a high conversion to amine-SecrI (11a) which was essentially fully kidney-selective with no detectable plasma concentrations (Table 5B). The selectivity towards kidney appeared to decrease over time, probably due to fast clearance and re-equilibration of the amine-SecrI (11a). However, the high selectivity at earlier time-points assured that the total exposure over time was much higher in the kidney compared to the liver. The Ac-α-Glu-SecrI (15a) prodrug was converted to a much lower extent than the Ac-γ-Glu-SecrI (13a) to amine-SecrI (11a) and more in the liver (400%) than in the kidney (Table 5C). The H-α-Glu-SecrI (15b) showed the overall highest conversion to amine-SecrI (11a), but again more efficiently in the liver (700% at 0.5 h) than in the kidney (Table 5D). In summary, these results clearly demonstrated that the low plasma exposure of Ac-γ-Glu-SecrI (13a) was due to a rapid uptake into liver and kidney followed by kidney-selective hydrolysis to form amine-SecrI (11a) rather than direct hydrolysis in plasma, since amine-SecrI (11a) stayed at all time-points below the limit of quantitation in plasma. We never observed significant amounts of hydrolysis of the linker in 11a to the free antagonist 8.

Example 15

Effects of Amine-SecrI (11a) and its Prodrug Ac-γ-Glu-SecrI (13a) in a Mouse Model of Acute Kidney Injury Animal Model of Induced Acute Kidney Disease All experiments with animals were conducted in accordance with federal and local regulation at the respective study location. Kidney injury was induced by intraperitoneal (i.p). injection of aristolochic acid (AA, Sigma-Aldrich, 1×5 mg/kg) in 10 weeks old BALB/c male mice. The γ-secretase inhibitors prodrugs were diluted in NaCl 0.9% and administered i.p., starting one day before the injection of AA (day −1) and then twice daily until day 6 evening (n=5 mice/experimental group). At day 7 morning (12 h after the last prodrug injection), blood was collected and the mice were sacrificed to remove the liver and both kidneys. The kidneys were cut in four fragments. One fragment was immediately frozen in liquid nitrogen, one fragment was included in OCT (Tissue-Tek, VWR International, Switzerland) and frozen, one fragment was frozen at −80° C. and one fragment was fixed in 4% paraformaldehyde and included in paraffin.

Immunohistochemistry of Notch1 and Cleaved Notch1 in the Kidneys of Mice Exposed to Aristolochic Acid and Ac-γ-Glu-SecrI (13a)

OCT-embedded frozen kidneys were cut at 7 μm. The sections were air dried, fixed for 10 min in cold (−20° C.). methanol, rinsed in PBS 0.1% Triton x-100 (PBS/Triton), and blocked for 30 min with PBS/Triton containing 5% bovine serum albumin (BSA). The rabbit anti-Notch1 antibody (D1E11, diluted 1/50) and the rabbit anti-cleaved

TABLE 5

Distribution of the active drugs in plasma, liver and kidney of non-diseased mice after i.p. injection (10 mg/kg) of the γ-secretase inhibitor analogues.

| Time (h) | Plasma (ng/mL) | | Liver (ng/g) | | Kidney (ng/g) | |
|---|---|---|---|---|---|---|
| A: Administration of active drug amine-SecrI (11a) | | | | | | |
| | 11a | | 11a | | 11a | |
| 0.5 | 97.8 | | 70000 (450) | | 15500 (100) | |
| 4 | 1.32 | | 3000 (250) | | 1200 (100) | |
| 7 | 2.08 | | 1200 (290) | | 420 (100) | |
| B: Administration of prodrug Ac-γ-Glu-SecrI (13a) | | | | | | |
| | 13a | formed 11a | 13a | formed 11a | 13a | formed 11a |
| 0.5 | 4.88 | BQL | 3570 | 82.1 (0.7) | 1032 | 12240 (100) |
| 4 | BQL | BQL | 625 | 39.8 (42) | 16.6 | 94.6 (100) |
| 7 | BQL | BQL | 22.3 | 18.0 (105) | BQL | 17.2 (100) |
| C: Administration of prodrug Ac-α-Glu-SecrI (15a) | | | | | | |
| | 15a | formed 11a | 15a | formed 11a | 15a | formed 11a |
| 0.5 | 573 | 18.7 | 7220 | 1258 (400) | 7536 | 315 (100) |
| 4 | BQL | 3.92 | 2850 | 177 (710) | 81 | 24.7 (100) |
| 7 | 6.29 | 0.46 | 737 | 37 (310) | 33.8 | 11.7 (100) |
| D: Administration of prodrug H-α-Glu-SecrI (15b) | | | | | | |
| | 15b | formed 11a | 15b | formed 11a | 15b | formed 11a |
| 0.5 | 3.67 | 36.6 | 277 | 16926 (700) | 8.51 | 2371 (100) |
| 4 | BQL | 1 | 60.7 | 2385 (630) | BQL | 380 (100) |
| 7 | BQL | BQL | 5.78 | 464 (390) | BQL | 119 (100) |

Plasma and tissue concentrations of administered compound (A-D) and formed amine-SecrI (11a) (B-D) were determined following 10 mg/kg i.p. administration in C57b/6 mice (no standard deviation given due to sparse sampling; n ≤ 3 mice per time point). Numbers in parentheses represent relative amounts with the exposure of 11a in kidney arbitrarily set at each time point to 100%. No free γ-secretase inhibitor 8 was detected.
BQL = below quantifiable limit.

Notch1 antibody (Val1744, diluted 1/50) were purchased from Cell Signaling, the biotinylated anti-rabbit antibody from Vector Laboratories (diluted 1/500) and streptavidin/HRP (diluted 1/500) from Dako. The primary antibodies were diluted in PBS containing 5% BSA and were incubated with the sections for 1 h at RT. Endogenous peroxidase and biotin were blocked using 3% $H_2O_2$ and Avidin/Biotin blocking kit (Vector Laboratories), respectively. The slides were rinsed with PBS/Triton three times and incubated for 1 h at RT with anti-rabbit biotin secondary antibody diluted in the same buffer as for primary antibodies. After three washes with PBS, slides were incubated with streptavidin/HRP antibody for 1 h at RT, then 3,3'diaminobenzidine (DAB, Dako) was added for 15 min. The slides were washed in distilled water, mounted in Aquamount and analyzed.

Effects of Amine-SecrI (11a) and its Prodrug Ac-γ-Glu-SecrI (13a) in a Mouse Model of Acute Kidney Injury To investigate potential nephroprotective effects of Notch blockade using γ-secretase inhibition and to evaluate the effects of our enzyme-targeted prodrug strategy, we used the in vivo AA mouse model of acute renal tubular damage. AA is a natural herbal component which is toxic to renal tubular epithelial cells, inducing apoptosis with impaired regeneration and autophagy of proximal tubular epithelial cells leading to progressive tubular atrophy and irreversible renal failure. The amine-SecrI (11a) which showed high kidney exposure in the single dose administration (Table 5A) was administered at 10 mg/kg b.i.d. and its prodrug Ac-γ-Glu-SecrI (13a) was administered at 30 mg/kg b.i.d., with treatment starting one day prior to the injection of a single dose of AA i.p. We chose to administer the prodrug (13a) at a higher dose compared to amine-SecrI (11a) to account for the relative differences in kidney exposures achieved for active amine-SecrI (11a) during single dose PK (Table 5 and description above). At day 7, 12 h after last prodrug administration, the animals were sacrificed and plasma, liver and kidney samples collected for exposure determination (Table 6) as well as immunohistochemistry (FIG. 3) for the evaluation of Notch1 and cleaved Notch1. We detected high exposure of kidney and liver with amine-SecrI (11a) even 12 h post administration (Table 6A) and a comparatively lower exposure of amine-SecrI (11a) in the Ac-γ-Glu-SecrI (13a) group (Table 6B and Table 6C), which confirmed our dose selections as predicted from the PK experiments (also compare with 7-h time-points in Table 5). There was a potential selectivity for kidney exposure in Ac-γ-Glu-SecrI (13a)-treated animals only (Table 6B), however difficult to ascertain due to the late time-point. We also observed a small selectivity in the AA- and Ac-γ-Glu-SecrI (13a)-treated animals (Table 6C), suggesting that the effect of prodrug cleavage was still working in diseased kidneys. In the immunohistochemistry evaluation (FIG. 3), we observed up-regulation of Notch1 and cleaved Notch1 in diseased kidneys of AA-treated mice in the absence of the prodrug, which were reduced in AA-exposed and (11a)-treated or (13a)-treated mice (FIG. 3), suggesting a beneficial effect of the N-acylase-γ-GT-targeted γ-secretase prodrug in controlling the activation of the Notch pathway in acute kidney injury. Neither (11a) nor (13a) injected alone induced any modification of Notch or cleaved Notch levels in the kidneys of healthy wild-type mice (results not shown). Overall, these experiments demonstrated that the N-acetyl-γ-glutamyl prodrug (13a) was cleaved to the amine-SecrI (11a), but not to the free γ-secretase inhibitor (8) in vivo, was kidney-specific and was active after cleavage in vivo by enzyme(s) expressed in acutely injured renal tubular cells to control the activation of the Notch pathway.

TABLE 6

Distribution of the active drugs in plasma, liver and kidney of aristolochic-exposed mice after i.p. injection of the γ-secretase inhibitor analogues.

| Time (h) | Plasma (ng/mL) | | Liver (ng/g) | | Kidney (ng/g) | |
|---|---|---|---|---|---|---|
| A: Administration of active drug amine-SecrI (11a) and AA | | | | | | |
|  | 11a | 8 | 11a | 8 | 11a | 8 |
| 13 | 7.2 | BQL | 1246 (68) | 100 | 1826 (100) | 11.3 |
| B: Administration of prodrug Ac-γ-Glu-SecrI (13a) | | | | | | |
|  | 13a | 11a | 13a | 11a | 13a | 11a |
| 13 | 6 | BQL | 19 | BQL | 11 | 124 (100) |
| C: Administration of prodrug Ac-γ-Glu-SecrI (13a) and AA | | | | | | |
|  | 13a | 11a | 13a | 11a | 13a | 11a |
| 13 | BQL | BQL | 155 | 39 (63) | 23 | 62 (100) |

Plasma and tissue concentrations of administered compound (Table 6A-C) and formed free γ-secretase inhibitor (8) (Table 6A) or amine-SecrI (11a) (Table 6B-C) were determined following 8-day repeated i.p. administration at 10 mg/kg b.i.d. (Table 6A) or 30 mg/kg b.i.d. (Table 6B-C) in AA-treated C57b/6 mice (AA-treatment on day 2). Numbers in parentheses represent relative amounts with the exposure of 11a in kidney arbitrarily set at each time point to 100%. No free γ-secretase inhibitor (8) was detected in (13a) treated mice. BQL=below quantifiable limit.

Example 16

Stability in Rats of SecrI (11a) and its Prodrugs

Ac-γ-Glu-SecrI (13a) and Ac-α-Glu-O-SecrI (13c) Pharmacokinetic Assessment in Male Wistar Rats We next determined the stability, tissue distribution and cleavage rate in plasma, liver and kidney of the designed prodrugs in male Wistar rats. In the in vivo screen, the kinetics and distribution of the prodrugs Ac-γ-Glu-SecrI (13a) and Ac-γ-Glu-O-SecrI (13c) were compared with the active γ-secretase inhibitor SecrI (8). After i.v. administration in male Wistar rats, the disappearance of the prodrugs and the formation of the active amine-SecrI (11a), amine-O-SecrI (11b) and SecrI (8) were compared in plasma, liver and kidney (Table 7A-C). First, we determined the pharmacokinetics (PK) behavior of SecrI (8) following i.v. administration (Table 7A). As expected, SecrI (8) had good plasma exposure and rapid plasma clearance. Liver and kidney exposure were much higher, with same exposure in liver and kidney. As expected for the prodrug Ac-γ-Glu-SecrI (13a), we saw at 0.25 h a high conversion to amine-SecrI (11a) which was essentially fully kidney-selective with no detectable plasma concentrations of the active γ-secretase inhibitors 11a and 8 (Table 7B). The selectivity towards kidney stayed constant over time. The carbonate analogue Ac-γ-Glu-O-SecrI (13c) prodrug was converted to a lower extent than the Ac-γ-Glu-SecrI (13a) to amine-O-SecrI (11b) but more to the linker free γ-secretase inhibitor 8 (Table 7C). Amine-O-SecrI (11b) had at early time points a very good kidney selectivity but the more prominent free γ-secretase inhibitor 8 had at all time points only a moderate kidney selectivity. Both active γ-secretase inhibitors 8 and 11b showed detectable concentrations at early time points in plasma proving that carbonate-linkers are less suitable for optimal kidney selectivity in animals. In summary, these results clearly demonstrated that the low plasma exposure of Ac-γ-Glu-SecrI (13a) was due to good stability in plasma, a rapid uptake into liver and kidney followed by kidney-selective hydrolysis to form amine-SecrI (11a) rather than direct hydrolysis in plasma.

For Ac-γ-Glu-SecrI (13a) we never observed significant amounts of hydrolysis of the linker in 11a to the free γ-secretase inhibitor 8. In contrast, the closely related Ac-γ-Glu-O-SecrI (13c) prodrug was significantly converted to the linker-free γ-secretase inhibitor 8, unfortunately also in plasma. This demonstrates that specific combinations of linkers and prodrug mechanisms are required to achieve selective transport and cleavage in order to avoid unwanted plasma and/or tissue exposure with active γ-secretase inhibitors.

TABLE 7

Distribution of the active drugs in plasma, liver and kidney of non-diseased rats after i.v. injection of the γ-secretase inhibitor analogues

| Time (h) | Plasma (ng/mL) | | | Liver (ng/g) | | | Kidney (ng/g) | | |
|---|---|---|---|---|---|---|---|---|---|
| A: Administration of active drug SecI (8) (3.5 mg/kg) | | | | | | | | | |
| | 8 | | | 8 | | | 8 | | |
| 0.25 | 964.5 | | | 3100 (93) | | | 3320 (100) | | |
| 1.25 | 197.5 | | | 852 (101) | | | 844 (100) | | |
| 2.2 | 39.7 | | | 298.4 (133) | | | 225.2 (100) | | |
| 7 | 18.4 | | | 116.4 (126) | | | 92.4 (100) | | |
| B: Administration of prodrug Ac-γ-Glu-SecrI (13a) (1.6 mg/kg) | | | | | | | | | |
| | 13a | formed 11a | | 13a | formed 11a | | 13a | formed 11a | |
| 0.25 | 295 | BQL | | 400 | 5.7 (1) | | 188 | 481 (100) | |
| 0.5 | 11.2 | BQL | | 33.4 | 3.1 (3) | | 12.7 | 106 (100) | |
| 4 | BQL | BQL | | BQL | 0.5 (8) | | 16.6 | 6.3 (100) | |
| 7 | BQL | BQL | | BQL | BQL (0) | | BQL | 5.2 (100) | |
| C: Administration of prodrug Ac-γ-Glu-O-SecrI (13c) (1.5 mg/kg) | | | | | | | | | |
| | 13c | formed 11b | formed 8 | 13c | formed 11b | formed 8 | 13c | formed 11b | formed 8 |
| 0.25 | 53 | BQL | 18.7 | 196 | 7.7 (7) | 63.0 (36) | 20.5 | 115 (100) | 174 (100) |
| 0.5 | 4.6 | BQL | 5.1 | 32.3 | 1.8 (4) | 26.2 (27) | 3.8 | 48.3 (100) | 96.0 (100) |
| 4 | BQL | BQL | BQL | BQL | 4.6 (350) | 5.3 (16) | BQL | 1.3 (100) | 33.2 (100) |
| 7 | BQL | BQL | BQL | BQL | 2.4 (240) | 12.5 (43) | BQL | 1.0 (100) | 29.4 (100) |

Plasma and tissue concentrations of administered compound (A-C) and formed amine-SecrI (11a), amine-O-SecrI (11b) or SecrI (8) (B-C) were determined following i.v. administration in rats (no standard deviation given due to sparse sampling; n≤3 rats per time point). Numbers in parentheses represent relative amounts with the exposure of kidney arbitrarily set at each time point to 100%. No free γ-secretase inhibitor 8 was detected after Ac-γ-Glu-SecrI (13a) administration. BQL=below quantifiable limit.

The invention claimed is:

1. A conjugate of formula (I):

or a pharmaceutically acceptable salt thereof, wherein A is a γ-secretase inhibitor moiety of formula (A2):

(A2)

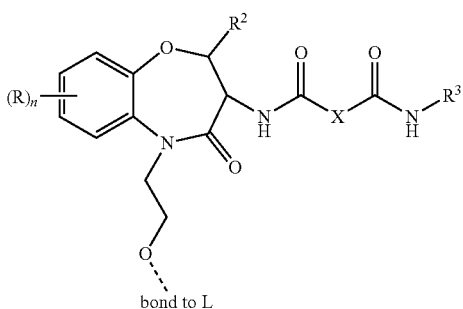

X is —CR⁴R⁴'— or —CR⁴R⁴'—O—;
R is halogen, $C_{1-7}$ alkyl or $C_{1-7}$ alkyl substituted by halogen;
R' is $C_{1-7}$ alkoxy, hydroxy or amino;
R² is hydrogen, $C_{1-7}$ alkyl, $C_{1-7}$ alkyl substituted by halogen or hydroxy, or is benzyl or $C_{3-8}$ cycloalkyl;
R³ is $C_{1-7}$ alkyl, $C_{1-7}$ alkyl substituted by halogen, is benzyl, benzyl substituted by two halogen, is —(CH₂)$_m$—$C_{3-8}$cycloalkyl or —(CH₂)$_m$-pyridinyl;
R⁴ and R⁴' are independently from each other hydrogen, halogen, $C_{1-7}$ alkyl, $C_{1-7}$ alkyl substituted by hydroxy, $C_{1-7}$ alkoxy, or hydroxy;
n is 0, 1 or 2;
m is 0, 1 or 2;
with the proviso that at least one of R¹, R², R⁴ or R⁴' is hydroxy or $C_{1-7}$ alkyl substituted by hydroxy;
L is a cleavable linker moiety of formula (L1):

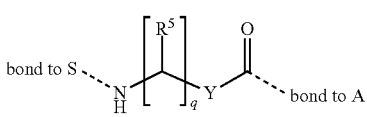

(L1)

wherein
Y is void, O or NH;
R⁵ is hydrogen, halogen, $C_{1-7}$ alkyl, or $C_{1-7}$ alkoxy;
q is 1, 2, 3 or 4; and
S is a peptidase-specific substrate of formula (S1):

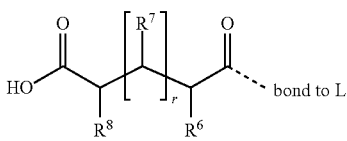

(S1)

wherein
R⁶ is hydrogen, $C_{1-7}$ alkyl, —NH₂ or —NH—C(O)—$C_{1-7}$ alkyl;
each R⁷ is independently selected from hydrogen, halogen, $C_{1-7}$ alkyl, or $C_{1-7}$ alkoxy;
R⁸ is hydrogen, $C_{1-7}$ alkyl, —NH₂ or —NH—C(O)—$C_{1-7}$ alkyl;
r is 0, 1, 2 or 3;
with the proviso that at least one of R⁶ or R⁸ is —NH₂ or —NH—C(O)—$C_{1-7}$ alkyl.

2. The conjugate of claim 1, wherein X is —CH₂—, —CHCH₃—, —CH(CH₂CH₃)—, —C(CH₃)₂—, —C(CH₃)(OH)—, —C(CH₂CH₃)(OH)—, —CH(OCH₃)— or —C(CH₃)₂—O—.

3. The conjugate of claim 1, wherein R is halogen.
4. The conjugate of claim 1, wherein R² is $C_{1-7}$ alkyl, $C_{1-7}$ alkyl substituted by hydroxy, or $C_{3-8}$ cycloalkyl.
5. The conjugate of claim 1, wherein R³ is $C_{1-7}$ alkyl substituted by halogen.
6. The conjugate of claim 1, wherein R³ is $C_{1-7}$ alkyl substituted by 3 or 5 fluoro.
7. The conjugate of claim 1, wherein moiety A is selected from the group consisting of:
N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2,2-dimethyl-N'-(2,2,3,3,3-pentafluoro-propyl)-malonamide;
N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide;
N-((6R,7S)-6-Cyclopropyl-2-fluoro-8-oxo-6,7,8,9-tetrahydro-5-oxa-9-aza-benzocyclohepten-7-yl)-2-hydroxy-2-methyl-N'-(2,2,3,3,3-pentafluoro-propyl)-malonamide;
(S)—N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide;
(R)—N-[(6R,7S)-2-Fluoro-9-(2-hydroxy-ethyl)-6-methyl-8-oxo-6,7,8,9-tetrahydro-5-oxa-9-aza-benzocyclohepten-7-yl]-2-hydroxy-2-methyl-N'-(2,2,3,3,3-pentafluoro-propyl)-malonamide;
(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide;
(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,3,3,3-pentafluoro-propyl)-malonamide;
(S)—N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide;
(R)—N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide;
(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide;
(R or S)N-[(6R,7S)-2-Fluoro-6-methyl-8-oxo-9-(2,2,2-trifluoro-ethyl)-6,7,8,9-tetrahydro-5-oxa-9-aza-benzocyclohepten-7-yl]-2-hydroxy-2-methyl-N'-(3,3,3-trifluoro-propyl)-malonamide;
N-[(6S,7R)-6-Ethyl-2-fluoro-8-oxo-9-(2,2,2-trifluoro-ethyl)-6,7,8,9-tetrahydro-5-oxa-9-aza-benzocyclohepten-7-yl]-2,2-dimethyl-N-(2,2,3,3,3-pentafluoro-propyl)-malonamide;
(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide;
(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,2-trifluoro-ethyl)-malonamide;
(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide;

(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(2,2,3,3,3-pentafluoro-propyl)-malonamide;

(R or S)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide;

(S or R)-2-Ethyl-N-((6R,7S)-6-ethyl-2-fluoro-8-oxo-6,7,8,9-tetrahydro-5-oxa-9-aza-benzocyclohepten-7-yl)-2-hydroxy-N-(3,3,3-trifluoro-propyl)-malonamide;

(R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide;

(S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,2-trifluoro-ethyl)-malonamide;

(R or S)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide;

(S or R)-2-Ethyl-N-[(6R,7S)-6-ethyl-2-fluoro-8-oxo-9-(2,2,2-trifluoro-ethyl)-6,7,8,9-tetrahydro-5-oxa-9-aza-benzocyclohepten-7-yl]-2-hydroxy-N-(2,2,3,3,3-pentafluoro-propyl)-malonamide;

N-[(6R,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

N-[(6S,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

(S)—N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(R)—N-[(6S,7R)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(S)—N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

(R)—N-[(6R,7S)-2-Fluoro-6-(2-hydroxy-ethyl)-8-oxo-6,7,8,9-tetrahydro-5-oxa-9-aza-benzocyclohepten-7-yl]-2-hydroxy-2-methyl-N'-(2,2,2-trifluoro-ethyl)-malonamide;

N-[(6R,7R) or (6S,7S)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

N-[(6S,7S) or (6R,7R)-2-Fluoro-6-(2-hydroxy-ethyl)-8-oxo-6,7,8,9-tetrahydro-5-oxa-9-aza-benzocyclohepten-7-yl]-2,2-dimethyl-N'-(2,2,3,3,3-pentafluoro-propyl)-malonamide;

(S)—N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide; and (R)—N-[(6R,7S)-6-Ethyl-2-fluoro-8-oxo-9-(2,2,2-trifluoro-ethyl)-6,7,8,9-tetrahydro-5-oxa-9-aza-benzocyclohepten-7-yl]-2-hydroxy-2-methyl-N'-(2,2,2-trifluoro-ethyl)-malonamide.

8. The conjugate according to claim 1, wherein Y is NH.

9. The conjugate of claim 1, wherein $R^5$ is hydrogen.

10. The conjugate of claim 1, wherein q is 2.

11. The conjugate according to claim 1, wherein one of $R^6$ or $R^8$ is —$NH_2$ or —NH—C(O)—$C_{1-7}$ alkyl and the other one of $R^6$ or $R^8$ is hydrogen or $C_{1-7}$ alkyl.

12. The conjugate of claim 1, wherein $R^7$ is hydrogen and r is 1.

13. The conjugate of claim 1 selected from the group consisting of:

(S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;

(S)-2-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;

(S)-4-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid;

(S)-4-amino-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonylamino)ethylamino)-5-oxopentanoic acid; and (S)-2-acetamido-5-(2-((2-((2R,3S)-7-fluoro-3-((S)-2-hydroxy-2-methyl-3-oxo-3-(2,2,3,3,3-pentafluoropropylamino)propanamido)-2-methyl-4-oxo-3,4-dihydrobenzo[b][1,4]oxazepin-5(2H)-yl)ethoxy)carbonyloxy)ethylamino)-5-oxopentanoic acid;

or a pharmaceutically acceptable salt thereof.

14. A pharmaceutical composition comprising a conjugate of claim 1 and one or more pharmaceutically acceptable excipients.

* * * * *